(12) United States Patent
Ben-David et al.

(10) Patent No.: US 6,573,050 B1
(45) Date of Patent: Jun. 3, 2003

(54) TREATMENT, DIAGNOSIS AND EVALUATION OF ANTI-CANCER THERAPY RESISTANCE IN MELANOMA

(75) Inventors: Yaacov Ben-David, Toronto (CA); Robert S. Kerbel, Toronto (CA); Brian J. Pak, Toronto (CA)

(73) Assignee: Sunnybrook & Women's College Health Sciences Centre, Toronto (CA)

( * ) Notice: Subject to any disclaimer, the term of this patent is extended or adjusted under 35 U.S.C. 154(b) by 0 days.

(21) Appl. No.: 09/697,074

(22) Filed: Oct. 27, 2000

Related U.S. Application Data

(60) Provisional application No. 60/162,227, filed on Oct. 29, 1999.

(51) Int. Cl.$^7$ .......................... C07H 21/04; C12Q 1/68; C12N 15/85; C12N 15/86
(52) U.S. Cl. .......................... 435/6; 435/325; 435/375; 536/24.5
(58) Field of Search .......................... 435/375; 514/44; 536/23.1, 23.5, 24.5

(56) References Cited

U.S. PATENT DOCUMENTS

| | | | |
|---|---|---|---|
| 5,130,145 A | 7/1992 | Oftebro et al. | |
| 5,252,342 A | 10/1993 | Howell et al. | |
| 5,340,565 A | 8/1994 | Pero | |
| 5,359,047 A | 10/1994 | Donahue et al. | |
| 5,434,046 A | 7/1995 | Enns et al. | |
| 5,646,011 A | 7/1997 | Yokoyama | |
| 5,705,336 A | 1/1998 | Reed et al. | |
| 5,831,016 A | 11/1998 | Wang et al. | |
| 5,840,839 A | 11/1998 | Wang et al. | |
| 5,843,674 A | 12/1998 | Takimoto et al. | |
| 5,846,725 A | 12/1998 | Yokoyama | |
| 5,858,674 A | 1/1999 | Yokoyama | |
| 6,054,467 A | 4/2000 | Gjerset | |
| 6,083,703 A | * 7/2000 | Wang et al. | .................. 435/6 |

FOREIGN PATENT DOCUMENTS

WO 9736005 A1 10/1997

OTHER PUBLICATIONS

Antisense '97: A roundtable on the state of the industry. Nature Biotechnol. 15 (1997): 519–524.*
Crooke, S. T. Vitravene—Another piece in the mosaic. Antisense & Nucleic Acid Drug Devel. 8(1998), vii–viii.*
Gewirtz et al. Facilitating oligonucleotide delivery: Helping antisense deliver on its promise. Proc. Natl. Acad. Sci. USA 93(1996): 3161–3163.*
Jen et al. Suppression of gene expression by targeted disruption of messenger RNA: Available options and current strategies. Stem Cells 18 (2000): 307–319.*
Report and recommendations of the panel to assess the NIH investment in research on gene therapy, Orkin and Motulsky, co–chairs. National Institutes of Health (12/95).* Rojanasakul, Y. Antisense oligonucleotide therapeutics: Drug delivery and targeting. Adv. Drug Delivery Rev. 18(1996):115–131.*
Stull et al. Antigene, ribozyme,and aptamer nucleic acid drugs: Progress and prospects. Pharm. Res. 12(1995): 465–483.*
Stephen F. Altschul et al.; Basic Local Alignment Search Tool; (May 15, 1990).
Bruce K. Armstrong et al.; Cutaneous Melanoma; Cancer Surveys vol. 19; (1994) Imperial Cancer Research Fund.
Maria Rosa Bani et al.; Cancer Research vol. 56, pp. 3075–3086, (Jul. 1, 1996).
Christopher Bartholomew et al.; Molecular and Cellular Biology, (Apr. 1991), pp. 1820–1828.
Samuel D. Bernal et al.; Molecular and Cellular Biochemistry vol. 95, pp. 61–70, (1990).
Grace Bradley et al.; Mechanism of multidrug resistance; vol. 948 (1988), pp. 87–128.
Daniela Gornati et al.; Anti–Cancer Drugs (1997), vol. 8, pp. 509–516.
Ian J. Jackson et al.; The EMBO Journal vol. 11, No. 2, pp. 527–535, (1992).
Burkhard Jansen et al.; Nature Medicine, vol. 4, No. 2, pp. 232–234, (Feb. 1998).
Koichiro Kameyama et al.; The Society for Investigative Dermatology, Inc., pp. 126–131, (1993).
Hiroshi Kuroda et al.; Int. J. Cancer, vol. 47, pp. 732–737, (1991).
U.K. Laemmli; MRC Laboratory of Molecular Biology, Hills Road, Cambridge; Nature vol. 227, pp. 680–685, (Aug. 15, 1970).
Aurelio Lorico et al.; Cancer Research vol. 48, pp. 2036–2041, (Apr. 15, 1988).
Shi–Jiang Lu et al.; Cancer Research vol. 55, pp. 1139–1145, (Mar. 1, 1995).
Brett P. Monia et al.; Nature Medicine vol. 2, No. 6, pp. 668–675, (Jun. 1996).
P.A. Riley; Int. J. Biochem. Cell Biol. vol. 29, No. 11, pp. 1235–1239, (1997).
Joseph Sambrook et al.; Molecular Cloning, A Laboratory Manual, $2^{nd}$ Edition, (1989).
A. Webb et al.; The Lancet vol. 349, pp. 1137–1141, Apr. 19, 1997.

* cited by examiner

*Primary Examiner*—Sean McGarry
*Assistant Examiner*—Karen A. Lacourciere
(74) *Attorney, Agent, or Firm*—Kathleen E. Marsman; Borden Ladner Gervais LLP

(57) ABSTRACT

The invention relates to overcoming anti-cancer therapy resistance in melanoma by regulation of the expression of tyrosinase related protein 2 (TYRP2). Treatment of melanoma with anti-cancer therapy may be negatively impacted by anti-cancer resistance of melanoma cells. Altering expression of TYRP2 in melanoma cells can enhance efficacy of anti-cancer therapies, such as chemotherapy and radiotherapy. Methods for treatment of melanoma are disclosed, as well as methods for diagnosis of anti-cancer therapy resistance, and methods for evaluating candidate anti-cancer therapies for melanoma. Down-regulation of TYRP2 expression or activity can be accomplished using a genetic therapy such as antisense therapy, or by using small molecules which regulate TYRP2.

8 Claims, 11 Drawing Sheets

* denotes number of animals in the 2 mg/kg group in which tumors completely disappeared

TREATMENT, DIAGNOSIS AND EVALUATION OF ANTI-CANCER THERAPY RESISTANCE IN MELANOMA

This application claims priority on provisional Application No. 60/162,227 filed on Oct. 29, 1999, the entire contents of which are hereby incorporated by reference.

FIELD OF THE INVENTION

The present invention relates to the treatment of melanoma, and in particular to treatment and diagnosis of anti-cancer therapy resistance in melanoma, as well as to the evaluation of resistance of a tumor or melanoma cells to anticer therapy.

BACKGROUND OF THE INVENTION

The tendency of tumors to express resistance to therapeutic agents remains a major obstacle in cancer treatment. Resistance mechanisms can be classified as either physiological or cellular (see Bradley et al. (1988) *Biochim. Biophys. Acta* 948:87–128). Physiological resistance mechanisms refer to properties of the tumor such as vascularity, that limit drug penetration into the rumor. Cellular resistance mechanisms involve the ability of individual cancer cells to undergo mutations or other types of genetic alterations which biochemically render these cells more resistant to the cytotoxic effects of anti-cancer therapeutic drugs. Such mechanisms include decreased drug uptake, increased drug efflux and increased drug detoxification. Resistant cancer cells may arise en masse in a de novo fashion prior to drug treatment ("intrinsic drug resistance") or they can be selected for by the drug ("acquired drug resistance"). One type of cancer which is well known for its intrinsic resistance to anti-ancer therapeutic drugs is malignant melanoma.

The incidence of malignant melanoma is increasing more rapidly than any other type of human cancer in North America (Armstrong et al. (1994) *Cancer Surv.* 19–20:219–240). Although melanoma is a curable cancer, the primary tumor must be removed at a very early stage of disease progression, i.e., before it has spread to distant sites. The presence of micrometastases can, and often do, lead to eventual symptomatic metastases. Because melanomas are intrinsically resistant to conventional methods of either chemotherapy or radiotherapy, it is virtually impossible to effectively treat such lesions in a clinically meaningful manner.

Intrinsic resistance to anti-cancer therapy, such as chemotherapeutic agents and radiotherapy, is a common characteristic of malignant melanoma and remains the main obstacle in clinical management of this disease. Thus, elucidating the molecular mechanisms underlying this intrinsic ability of melanoma tumors to resist anti-cancer therapy will lead to the development of clinically effective approaches to manage this disease.

Accordingly, there is considerable interest in elucidating the mechanisms by which cancer cells acquire resistance to anti-cancer therapies such as chemotherapy and radiation therapy. The rationale is that it ought to be possible to delay or prevent such resistance by pharmacologic means, provided more is known about the actual mechanisms involved. By way of example, it is known that some cancers may become resistant to commonly used drugs such as taxol, adriamycin, vincristine, and vinblastine by overexpressing a molecule known as P-glycoprotein on the cell surface. The function of P-glycoprotein is to pump potentially harmful drugs from the interior of the cell to the outside environment, to rid the cell of potentially harmful agents. Thus the pharmaceutical industry has put considerable resources into developing drugs which block the pumping action of P-glycoprotein in the hope of using such drugs as "chemosensitizers". In other words, a cancer cell which overexpresses P-glycoprotein, and which therefore is resistant to taxol, for example, might be made drug sensitive by exposure of the cells to taxol plus an agent which blocks P-glycoprotein function. An example of a drug for which melanoma is resistant to treatment with cis-diamminedichloroplatinum(II) (CDDP), a DNA-alkylating anti-cancer therapeutic agent used in the treatment of many types of cancer.

Studies over the past decade have demonstrated that CDDP exerts cytotoxic effects by covalently binding to DNA, so as to induce DNA strand breaks (single or double-strand breaks), disturb local DNA structures, and form DNA intra- and inter-strand crosslinks, which interfere with DNA replication and mRNA transcription, and leads to apoptotic cell death. Thus, it has been postulated that genes conferring resistance to CDDP are involved in various aspects of DNA repair, anti-apoptotic pathways and/or drug detoxification. Indeed, in certain CDDP resistant cancer cells, decreased intracellular accumulation of CDDP (Bernal et al. (1990) *Mol. Cell. Biochem.* 95:61–67), up-regulation of glutathione or glutathione-transferase activity, increased levels of metallothioneins, enhanced DNA repair activity, and decreased sensitivity to apoptosis have been corelated with the acquisition of drug resistance. However, the significance of these pathways in the intrinsic resistance of melanomas have not been clearly demonstrated. Furthermore, increases in the expression of these factors were not always detected in CDDP-resistant tumor cells, suggesting that other mechanisms may be involved in the expression of CDDP resistance.

It is known that tyrosinase-related protein 2 (TYRP2) and other melanocytic proteins, such as tyrosinase and TYRP1, are involved in the enzymatic processes that convert L-tyrosine to the pigment melanin in skin melanocytes. TYRP2 is also known as L-DOPAchrome tautomerase (dct) and is referred to in the literature under other abbreviations, such as Trp-2 and Trp2. TYRP2 is a member of the tyrosinase gene family and, along with tyrosinase and TYRP1, function in the conversion of L-tyrosine to melanin. Specifically, TYRP2 catalyzes the conversion of L-DOPAchrome to 5,6-dihydroxyindole-2-carboxylic acid in the melanin biosynthetic pathway in melanocytes. In melanoma cells, increased expression of TYRP2 is well documented. Indeed, TYRP2 has been shown to be recognized by cytotoxic T lymphocytes as a melanoma associated tumor antigen and as such is currently being analyzed as a vaccine.

Exploitation of the mechanisms for anti-cancer therapy resistance promises to provide new treatment opportunities. There is a need for methodologies which harness and traverse the mechanisms of chemotherapy and radiotherapy resistance to render melanoma cells susceptible to conventional anti-cancer therapies, as well as to those therapies as yet undiscovered. Further, there is a need for evaluative methodologies in order to determine relative susceptibility of a melanoma to a therapy.

U.S. Pat. No. 5,831,016 discloses TYRP2 as a human tumor antigen recognized by cytotoxic T lymphocytes. While this document discusses the use of TYRP2 peptides as antigens, it does not teach or suggest treatments involving down-regulation of the expression of the TYRP2 gene, nor does the document relate to inactivation or reduction of TYRP2 protein products in melanoma cells.

SUMMARY OF THE INVENTION

It is an object of the present invention to provide a method for treatment of melanoma, particularly by reducing or otherwise traversing anti-cancer therapy resistance, which method obviates or mitigates one or more of the shortcomings of prior art methodologies.

Further objects of the invention are to provide a method for diagnosis of anti-cancer therapy resistance, and a method for evaluation of resistance of melanoma to candidate anti-cancer therapies.

In accordance with the invention, there is provided a method of treating melanoma in a patient comprising the steps of: a) down-regulating TYRP2 in melanoma cells; and b) administering an effective dose of an anti-cancer therapy to the patient.

The invention also provides a method of determining anti-cancer therapy resistance in melanoma cells comprising the steps of: a) obtaining melanoma cells; b) measuring TYRP2 in the melanoma cells; c) comparing TYRP2 measured in step b) to a pre-determined standard to obtain a measurement of anti-cancer therapy resistance in the melanoma cells.

In accordance with a further embodiment, the invention provides a method of evaluating an anti-cancer therapy for resistance in melanoma cells comprising the steps of: a) obtaining an initial population of melanoma cells; b) altering TYRP2 in a sub-set of the initial population of melanoma cells to form an altered population of melanoma cells; c) providing an anti-cancer therapy to the initial population and the altered population of melanoma cells; d) comparing efficacy of the anti-cancer therapy in the altered population of melanoma cells relative to the initial population of melanoma cells.

The invention addresses a need for reduced resistance to anti-cancer therapy regimes such as chemotherapy and radiotherapy in melanoma cells so as to render melanoma cells drug or radiation sensitive. In addition, the invention addresses a need for diagnostic methods capable of evaluating the relative sensitivity of a melanoma to an anti-cancer therapy, which will advantageously assist in determining the most appropriate course of treatment. Further, the invention provides a method by which candidate anti-cancer therapies may be evaluated for TYRP2-mediated resistance, which will advantageously assist in identifying therapies to which melanoma cells are less likely to illustrate resistance.

BRIEF DESCRIPTION OF THE DRAWINGS

Embodiments of the present invention will now be described, by way of example only, with reference to the drawings wherein.

DETAILED DESCRIPTION OF THE INVENTION

Figure 1:
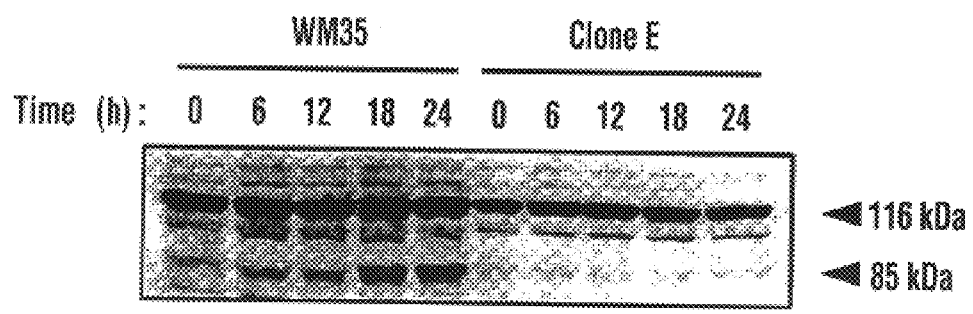
FIG. 1 shows relative amounts of cleavage of poly-ADP-ribose-polymerase (PARP) from a 116 kDa subunit to a 84 kDa subunit in WM35 cells and CDDP-resistant Clone E cells over 24 hours of CDDP treatment.

The invention relates to the treatment of melanoma through mediation of resistance to anti-cancer therapy, as well as to a method of diagnosing anti-cancer therapy resistance in melanoma cells. Further, the invention relates to a method for evaluating or screening anti-cancer therapy candidates for efficacy in melanoma treatment by evaluating the likelihood of a melanoma cell to illustrate resistance to the candidate therapy.

The invention is based on the surprising discovery that within a melanoma cell tyrosinase-related protein 2 (TYRP2) correlates to and effects the tendency of a melanoma cell to respond to anti-cancer therapy. By selectively targeting TYRP2, resistance to anti-cancer therapy can be reduced or traversed. The invention also provides methods for screening a melanoma, such as numor biopsy samples, for levels of TYRP2 in order to determine if these tumors will respond to an anti-cancer therapy.

New treatment methods for melanoma have been determined as a result of the recognition that the effectiveness of an anti-cancer therapies, such as chemotherapy or radiotherapy, is reduced in the presence of TYRP2 expression products. Advantageously, this aspect of the invention allows for the determination of a patient's relative sensitivity to an anti-cancer therapy on an individual basis by determining the relative degree of TYRP2 in melanoma cells derived from the patient. Anti cancer treatment regimes can then be designed individually with a higher probability of success for an individual patient.

The invention provides a method of treating melanoma in a patient comprising the steps of: a) reducing TYRP2 in melanoma cells; and b) administering an effective dose of an anti-cancer therapy to the patient.

By the phrase "reducing TYRP2 in melanoma cells" it is meant to alter the quantity, activity, effective amount of TYRP2, or quantity of reactants or products of TYRP2 activity within the cells. For example, TYRP2 can be reduced in a cell by down-regulating transcription of TYRP2, down-regulating translation of TYRP2, down-regulating expression of TYRP2, reducing TYRP2 protein content, or by reducing the activity of the TYRP2 protein in melanoma cells. Increasing activity of downstream pathways which may remove products of TYRP2 activity and decreasing activity of upstream pathways providing reactants for TYRP2 are also within the scope of this term.

The function of TYRP2 in converting L-DOPAchrome to DHICA, and further conversion by TYRP1 is considered a downstream mediator of TYRP2. The invention also relates to methods which involve regulation of DHICA through genetic therapies or small-molecule inhibitors which target DHICA as an alternative to targeting TYRP2 directly. This would have the same net effect of reducing TYRP2 in melanoma cells.

Ways in which TYRP2 can be reduced in melanoma cells include gene therapy, such as antisense therapy, or administration of small-molecule inhibitors of TYRP2. For example, an effective amount of an antisense oligonucleotide targeting TYRP2 mRNA could be administered to a patient by any acceptable means, for example through oral, enteral, parenteral, inhalation or injected delivery. An osmotic pump or a subcutaneous implant may be used to deliver ongoing therapy thereby avoiding the need for constant injection or ingestion. Further, a therapy can be administered by targeted delivery, for example in conjunction with an antibody or a melanoma-specific molecule.

For the optional embodiment in which reduction of TYRP2 is conducted by administration of an antisense oligonucleotide, the oligonucleotide may optionally be a phosphorothioated antisense oligonucleotide. Further, the antisense oligonucleotide may be one which targets the TYRP2 ATG translation initiation codon.

Antisense therapy may be used in the invention to mediate TYRP2 expression. Antisense oligonucleotides for use in the invention are any which are capable of binding along the length of the sequence of TYRP2 and effectively mediating TYRP2 expression, and thus TYRP2 protein levels. The TYRP2 sequence deposited in GenBank by Shibahara in 1993 (GenBank accession number D17547) is used herein to indicate particular exemplary portions of the sequence from which antisense sequences can be derived.

Table 1 provides exemplary antisense oligonucleotide sequences (SEQ ID NOs:1 to 10) for use in the invention to target TYRP2. The invention is not limited to these. Oligos for use in the invention may be any which bind to or otherwise inhibit TYRP2. Locations shown in Table 1 as "bp position" are provided which correspond to locations based on the Shibahara (1993) GenBank submission, having GenBank accession number D17547. The D17547 sequence is 2291 bp long with an open reading frame that spans nucleotides 415–1974. Nucleotides 415–483 represent a putative signal sequence.

TABLE 1

Exemplary Antisense Oligonucleotides based on TYRP2 Sequence

| by position | sequence (5'–3') | % GC | Tm | SEQ ID NO: |
|---|---|---|---|---|
| 512–493 | TCCACCGTCATGCAGACTCG | 60% | 75 | 1 |
| 519–500 | TAGGCTGTCCACCGTCATGC | 60% | 74 | 2 |
| 523–504 | TCACTAGGCTGTCCACCGTC | 60% | 71 | 3 |
| 567–548 | GACATTGGCCGACTCTGCAC | 60% | 74 | 4 |
| 1060–1041 | ATGCAGGTCCTTGATGTGAG | 50% | 68 | 5 |
| 1235–1216 | CTAATCAGAGTCGGATCGCT | 50% | 65 | 6 |
| 1581–1562 | ATCATTGGCGGCTGAATGTG | 50% | 74 | 7 |
| 1776–1757 | GCTGTAGCCAAGTTGGTCTG | 55% | 69 | 8 |
| 1997–1978 | CTCTTAGGTAAGGCATGAGC | 50% | 65 | 9 |
| 2033–2014 | TTGTCAGCGTCAGAACTGTG | 50% | 68 | 10 |

The sequences of Table 1 were chosen in part by utilizing Primer Designer™ v2.01, a shareware program obtained from Scientific & Educational Software. Some of the criteria used for oligo selection are as follows: (1) a % GC content ranging from 50 to 60%, (2) a Tm range of from 60 to 80 degrees Celsius, (3) hairpins (energy cutoff) of 0.0 kcal, (4) dimers are rejected if >=3 matches at 3' end, and if >=7 adjacent homologous bases, and (5) runs are rejected if runs of >=3 bases (anywhere) or if >=3 G or C at 3' end. Conservative substitutions within an oligo may also be made, provided that the resulting sequence binds adequately along TYRP2, as can be determined by one of skill in the art.

According to the invention, the step of reducing TYRP2 in melanoma cells can optionally include transfecting melanoma cells with an expression vector containing antisense TYRP2 cDNA, or treating melanoma cells with a small-molecule inhibitor of TYRP2.

The anti-cancer therapy which may be administered in conjunction with a reduction TYRP2 in melanoma cells may be any known or as-yet undiscovered therapy which stands to benefit from reduced TYRP2-mediated anti-cancer therapy resistance. Typically, anti-cancer therapies fall into the categories of chemotherapy and radiation therapy (or radiotherapy). Examples provided herein are do not in any way limit the invention thereto.

Among conventional chemotherapy agents, general sub-categories arise, which include alkylating agents, anti-metabolites, antibiotics, and anti-microtubule agents. Any of these therapies, or combinations thereof, which stand to benefit from reduced TYRP2-mediated anti-cancer therapy resistance can be used with the invention. Exemplary chemotherapy agents include cis-diamminedichloroplatinum (II) (CDDP), carboplatin, and methotrexate, as well as other DNA-damaging agents such as VP16, teniposide, daunorubicin, doxorubicin, dactinomycin, mitomycin, plicamycin, bleomycin, procarbazine, nitrosourea, cyclophosphamide, bisulfan, melphalan, chlorambucil, ifosfamide, merchlorehtamine, and anthracyclines.

Conventional anti-cancer radiotherapy regimes which may be combined with reduced TYRP2 according to the invention include ultraviolet radiation, such as TV(B) irradiation, gamma radiation, alpha particles, beta particles, X-rays and electron beams.

In one embodiment of the invention, there is provided a use of an antisense oligonucleotide targeting TYRP2 mRNA for preparation of a medicament for treatment of melanoma. The antisense may be any of those described above, and the medicament may be in any acceptable dosage form, such as in an ingestable pill, elixir, gel, inhalation formulation, aqueous or non-aqueous liquid formulation, injectable, time-release formulation in the form of a capsule or subcutaneous implant, or as a formulation for topical transdermal delivery. A pharmaceutically acceptable carrier appropriate for a given dosage form is included in any such medicament composition according to the invention. Exemplary antisense oligonucleotides selected for this use of the invention are those of SEQ ID NO:1 to SEQ ID NO:10.

According to an aspect of the invention, there is provided an oligonucleotide targeting TYRP2 mRNA for delivery to a patient receiving anti-cancer therapy for melanoma. Further, a composition containing an oligonucleotide targeting TYRP2 mRNA, in combination with a pharmaceutically acceptable carrier is also provided.

A method of determining anti-cancer therapy resistance in melanoma cells is provided according to the invention. This method comprises the steps of a) obtaining melanoma cells; b) measuring TYRP2 in the melanoma cells; c) comparing TYRP2 measured in step b) to a standard to obtain a measurement of anti-cancer therapy resistance in the melanoma cells.

By the phrase "measuring TYRP2" in melanoma cells, it is meant to evaluate a parameter indicative of TYRP2 potential, presence, or activity within melanoma cells. For example, the following parameters may be evaluated: transcription of TYRP2, translation of TYRP2, TYRP2 RNA, expression of TYRP2, TYRP2 protein content, activity of TYRP2 protein in melanoma cells, quantity of upstream molecules which serve as reactants for TYRP2 activity, or quantity of downstream products resulting from TYRP2 activity.

Comparison of a measured TYRP2 value with a standard value may be conducted in any conventional manner, either by obtaining control cells from the patient to be simultaneously measured as a control value, or by establishing a standard value, for example in the form of an acceptable range, on the basis of a control population. Such a value can be one which was pre-determined in advance of the obtaining step, and which may be available through established values, such as those published in peer-reviewed literature. The standard value may be adjusted to suit any sub-population, should variations in "normal" TYRP2 levels be found in any sub-population to be evaluated according to the invention.

According to the invention, melanoma cells may be obtained from a patient by obtaining a tissue biopsy sample through any conventional means available.

A further embodiment of the invention relates to a kit for screening melanoma cells for susceptibility to anti-cancer therapy comprising: a) a test assay for measuring TYRP2 in melanoma cells; and b) instructions for comparing a result obtained from the test assay with a standard TYRP2 value. The type of instructions available may be any which provide one of skill in the art with a standard value, such as a range, or with directions for obtaining a standard value from elsewhere, such as from the literature or from a control sample.

The kit can be used to determine an appropriate course of melanoma therapy based on expression of TYRP2. The kit can include a test assay for TYRP2 based on any conventional evaluation method, including activity-based assays, molecular biology (gel or blot) analysis, PCR, antibody binding, such as ELISA, or by DNA chip (oligo) binding.

The measurement obtained from the cells of the biopsy is compared to a known standard value, or to a value obtained from a control cell population, optionally derived from non-melanoma cells of the same patient which are analysed simultaneously.

The result obtained from the test kit provides information to assist a health care professional in determining the most appropriate course of treatment for the patient. If it appears that the melanoma cells have high TYRP2 expression, a physician may prefer to deliver a therapy to which resistance does not develop. Alternatively, if the melanoma cells illustrate regular TYRP2 expression, those therapies to which melanoma cells often illustrate resistance can be selected as the most effective course of treatment.

The invention also provides a method of evaluating an anti-cancer therapy for resistance in melanoma cells comprising the steps of: a) obtaining an initial population of melanoma cells; b) altering TYRP2 in a sub-set of the initial population of melanoma cells to form an altered population of melanoma cells; c) providing an anti-cancer therapy to the initial population and the altered population of melanoma cells; and d) comparing efficacy of the anti-cancer therapy in the altered population of melanoma cells relative to the initial population of melanoma cells. This method may be adapted to high-throughput screening for anti-cancer therapy candidates, for example in screening for drug candidates, or therapeutic regimes. The initial population of melanoma cells may be derived from a continuing source, such as commercially available cell lines. In this way, the invention provides a valuable resource for researchers working in the field of melanoma therapy.

By "altering TYRP2" in a sub-set of cells to form an altered population, it is meant to up-regulate or down-regulate transcription of TYRP2, translation of TYRP2, TYRP2 RNA, expression of TYRP2, TYRP2 protein content, activity of TYRP2 protein in melanoma cells, to increase or decrease the quantity of upstream molecules which serve as reactants for TYRP2 activity within a cell, or to increase or decrease the presence of downstream products resulting from TYRP2 activity within a cell. For example, up-regulation of TYRP2 expression to from an altered population of cells may be conducted by transfecting or infecting the initial population of cells with a virus encoding TYRP2.

The invention further relates to a melanoma cell altered as discussed above with regard to formation of an altered cell population. The cell so formed can be used for evaluation of efficacy of a candidate anti-cancer therapy. Such a cell may be one transfected with a TYRP2-containing vector.

Without wishing to be limited by theory, the results provided herein showing increased TYRP2 expression in CDDP-resistant clones suggest that TYRP2 may mediate resistance to DNA damaging agents in malignant melanoma, and that this function of TYRP2 may exist in addition to its well characterized function in melanogenesis.

The data provided herein demonstrate that the expression of the melanocyte-specific gene TYRP2 positively correlates with resistance to anti-cancer therapy, such as CDDP, both in vitro and in vivo. Further, the data demonstrate that the up-regulation of TYRP2 in human melanoma cells confers resistance to CDDP and other anti-cancer therapeutic agents. Additionally, down-regulation or inhibition of TYRP2 activity renders CDDP resistant melanoma cells CDDP sensitive. Accordingly, by exploiting the mechanisms by which TYRP2 functions to confer resistance to cell and the strategies to down-regulate or inhibit TYRP2 function provides unique methods for the treatment of malignant melanoma as described in greater detail below.

EXAMPLES

Exemplary embodiments of the invention will now be described in further detail. The examples should not be construed as limiting to the invention. Experimental materials and methods used throughout the examples are outlined below.

Cells and Culture Conditions. All human melanoma cell lines were generously provided by Dr. Meenhard Herlyn (Wistar Institute, Philadelphia, Pa.). The CDDP-resistant variants of WM35 (designated as Clone A to Clone I) were established by retroviral insertioual mutagenesis of WM35 cells as described previously (Lu et al. (1995) *Cancer Res.* 55:1139–1145). Cells were routinely maintained in RPMI 1640 (Life Technologies) supplement with 5% FBS (Life Technologies) at 37° C. in a humidified atmosphere of 95% air; 5% $CO_2$.

DNA Fragmentation Assay. Levels of apoptosis were determined by quantifying DNA fragmentation using the Cell Death Detection ELISA Plus kit (Boehringer Mannheim). Briefly, cells were plated in 96-well plates at a density of $1 \times 10^4$ cells/well and allowed to attach overnight. Cells were treated with 15 μM CDDP for 18 hours and then lysed. Cell lysates were transferred to streptavidin-coated plates and used for ELISA analysis using anti-bistone-biotin and anti-DNA POD antibodies.

Cytotoxicity Assay. The number of viable cells following a treatment was assessed using the CellTiter™ 96 Aqueous Non-Radioactive MTS Cell Proliferation Assay (Promega). Briefly, $1 \times 10^4$ cells/well were plated in 96-well plates, allowed to attach overnight and then administered therapeutic agents at various levels for 24 hours. Four hours prior to harvest, MTS/phenazine methosulfate was added to the cells and the number of variable cells was determined by measuring the quantity of formazan by spectrophotometric analysis at 490 nm.

Subtractive Hybridization. Subtractive hybridization was performed using the PCR-Select cDNA Subtraction Hybridization kit (vitrogen) as outlined by the manufacturer. Candidate cDNAs were cloned into pCR2.1 plasmid vectors by TA cloning (Invitrogen) and were sequenced and as probes for Northern blot analysis. DNA sequences were compared to previously reported sequences in the GenBank database using the BLAST algorithm (Altschul et al., (1990) J. Mol. Biol., 215, 403–410.).

Northern Blot Anulysis. Total RNA was extracted from cultured cells using the Trizol™ (Life Technologies) reagent according to the manufacturer's instructions. RNA extracts were quantified by spectrophotometric analysis and 10 μg of each extract were fractionated on 1% agarose/formaldehyde gels and transferred to nylon filters (ZetaProbe™, BioRad Laboratories) as described previously in Sambrooke et al., (1989) in Molecular Cloning: A Laboratory Manual, 2nd edition, Cold Spring Laboratory Press: Cold Spring Harbour. Prehybridization and hybridization with $^{32}$P-labeled cDNA probes were preformed at 42° C. in 50% formamide, 5×SSPE, 1×Denhardt's solution, 5% dextran sulfate and 1% SDS. Following hybridization, blots were washed with high stringency at 65° C. and exposed onto X-ray film.

SDS-PAGE and Western Blot Analysis. Cell lysates were prepared using lysis buffer consisting of 50 mM Tris, pH 7.4, 50 mM NaCl, 2 mM $MgCl_2$, 1 mM EDTA, 05% IDEPAL CA-630 and protease inhibitors (0.1 mM PMSF, 100 μM sodium vanadate, 20 μg/ml leupeptin, 20 mM $NaF_2$, 1 mM benzamide). Protein concentrations were determined by the Bradford assay (BioRad Laboratories) and equivalent quantities of protein (25 μg) were resolved by SDS-polyacrylamide gel electrophoresis (Laemmli (1970) *Nature*, 227, 680–685). Following electrophoresis, proteins were transferred to polyvinylidene difluoride membranes (Immobilon-P™, Millipore) and incubated with polyclonal antibodies at the appropriate dilutions in 5% milk powder. Membranes were then incubated with a horseradish-peroxidase conjugated goat anti-rabbit antibody (1:5000 dilution) and immunoreactive sites were detected by enhanced chemiluminescence (Amersham). The αPEP8 polyclonal antibody against human TYRP2 (provided by Dr. Vincent Hearing, Western General Hospital, Edinburgh, UK) recognizes both the glycosylated (75 kDa) and precursor form (55 kDa) of TYRP2 (Jackson et al., (1992). *EMBO J.*, 11, 527–535.).

TYRP2 Transfectants of WM35. A 2.1 kb cDNA fragment of human TYRP2 (provided by Dr. Rick Sturm, University of Queensland, Australia) which included the complete open reading frame was cloned into the pcDNA3 expression vector (Invitrogen) and transfected into WM35 cells using Lipofectin (Life Technologies). Transfected cells were selected with 800 μg/ml geneticin (Life Technologies) for more than 2 weeks. Cells resistant to geneticin were individually subcloned and expanded in culture.

Example 1

Gene Identification and Establishment of CDDP Resistant Clones

With the initial goal of identifying gene(s) associated with drug resistance in human melanoma cells, the approach of retroviral insertional mutagenesis was utilized to establish clonal cell lines of a human melanoma that exhibited increased resistance to the cytotoxic effects of CDDP.

The general technique for the identification of the drug resistance gene was as follows: (i) use an amphotrophic retrovirus to infect a human melanoma cell line that showed some sensitivity to CDDP and select CDDP-resistant (variant) cells; ii) recover CDDP resistant clones and examine their DNA for evidence of common sites of proviral integration; (iii) once such sites are found, clone the flanking host genomic sequences and screen for transcriptional sequences located adjacent to the integration site.

This technique of retroviral insertional mutagenesis was applied on WM35 cells, an early stage CDDP sensitive human melanoma cell line. WM35 cells were infected with a replication defective amphotrophic murine stein cell virus (MSCV) retrovirus and the pooled cells were subsequently selected for CDDP resistance.

From this technique, nine independently derived clones, Clone A to Clone I, were obtained. Five of the nine clones (Clones B, D, E, F and G) had acquired the integration of a single virus at an identical site, designated as CDDP resistance locus-1 (CRL-1) as revealed by analysis of retroviral flanking sequences. Approximately a 2 to 3-fold increase in CDDP resistance was observed in the two clones analysed (E and G) compared to parental WM35 cells. Since changes in tumor sensitivities in the range of 2–5 fold can account for loss of tumor responsiveness to anti-cancer therapeutic drugs, this difference could be clinically significant (Kuroda et al. (1991) *Int. J. Cancer* 47:732–737). Accordingly, these data suggest that proviral integration at CRL-1 results in a mutation of host genes that is phenotypically manifested by an increase in CDDP resistance.

Example 2

Reduction of CDDP-Induced Apoptosis in CDDP-Resistant Cell Lines

The mechanism of action of CDDP, as well as other DNA alkylating agents ultimately involves generation of DNA damage and subsequently the induction of apoptosis. In order to determine if the increased resistance to CDDP in the retrovirally derived clones was associated with a reduction in CDDP-induced apoptosis, the levels of apoptosis in one of these clones (Clone E) relative to its parental WM35 cells were determined following treatment with 15 μM CDDP.

FIG. 1 shows a biochemical analysis of apoptosis in WM35 cells and the CDDP-resistant Clone E cells using Western blot analysis of the cleavage of the 116 kDa poly ADP-ribose polymerase (PARP) into its 85 kDa subunit. Increased cleavage of poly-ADP-ribose-polymerase (PARP) from the 116 kDa to the smaller 84 kDa subunit in WM35 cells was detected as early as 6 bours following 15 μM CDDP treatment. Increased levels of PARP cleavage was not evident in Clone E cells up to 24 hours.

Figure 2:
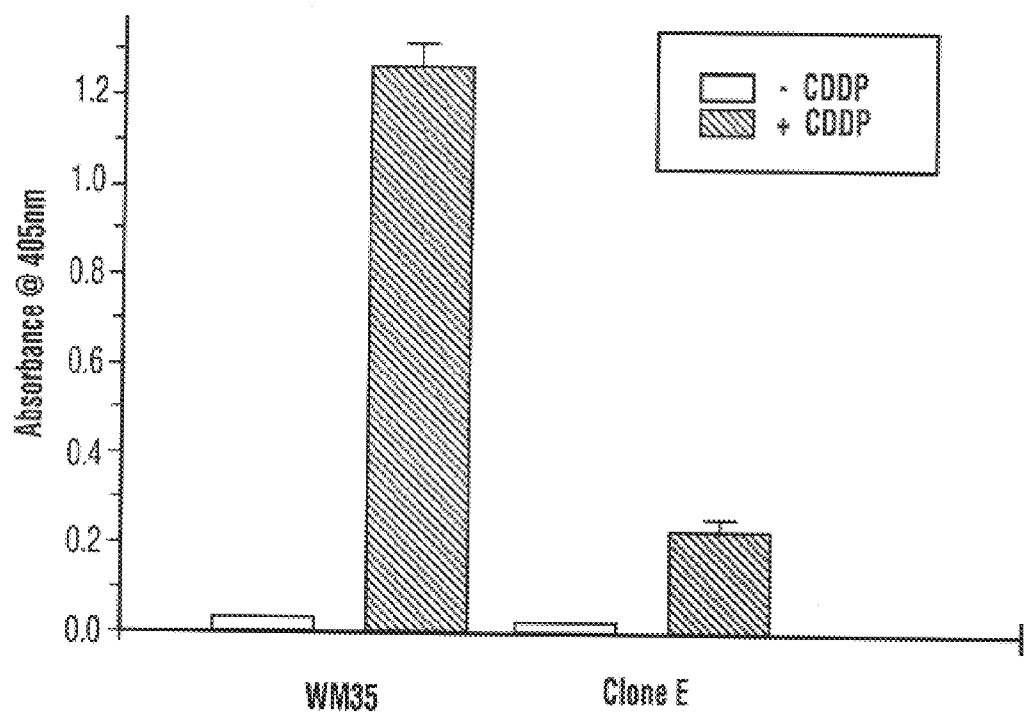
FIG. 2 illustrates relative amounts of DNA fragmentation, indicative of cell death, in WM35 cells and CDDP-resistant Clone E cells after 18 hours of CDDP treatment.

FIG. 2 illustrates DNA fragmentation analysis by ELISA using antibodies that recognize mono- and oligonucleotide fragments. Mono- and oligo-nucleosomes in the DNA of WM35 cells treated with 15 μM CDDP for 18 hours, were detected with a Cell Death ELISA Detection Kit (Boehringer Mannheim). The production of DNA 180 bp multimers was approximately 5 times greater in WM35 cells than in Clone E cells.

Both methods of analysis demonstrated a significant reduction in the levels of apoptosis in Clone E cells following exposure to 15 μM CDDP relative to WM35. Thus, these results suggest that the mutation(s) induced by proviral integration in the CDDP-resistant clones altered the apoptotic response of the cells to CDDP, possibly by reducing the amount of CDDP-induced DNA damage of by increasing their DNA repair capacity.

Example 3

Cross Resistance of CDDP Resistant Clones to Carboplatin and Methotrexate but not Taxol A feature of many CDDP resistant malignant cells in other systems is their cross-resistance to a variety of anti-cancer therapeutic agents such as 5-fluorouracil, melphalan, amsacrine, 6-mercaptopurine, beomycin, adriamycini and mitoxantrone (see for example, Gornati et al. (1997) *Anticancer Drugs* 8:509–516). In order to determine in the CDDP-resistant clones also exhibit cross-resistance to other drugs, Clone E and Clone G cells were created with various doses of carboplatin, methotrexate and taxol. The mechanism of action of carboplatin is similar to that of CDDP, and forms DNA adducts and cross-links. Methotrexate is a specific inhibitor of the enzyme dihydrofolate reductase (DHFR) and acts by limiting the synthesis of purine and pyrimidine nucleotides, thereby impairing DNA repair and eventually leading to methotrexate-induced single and double stand breaks (Lorico et al. (1988) *Cancer Res.* 48:2036–2041.). On the other hand, taxol induced apoptosis involves the stabilization of microtubules, which blocks cells in the G2/M checkpoint of the cell cycle.

Figure 3:
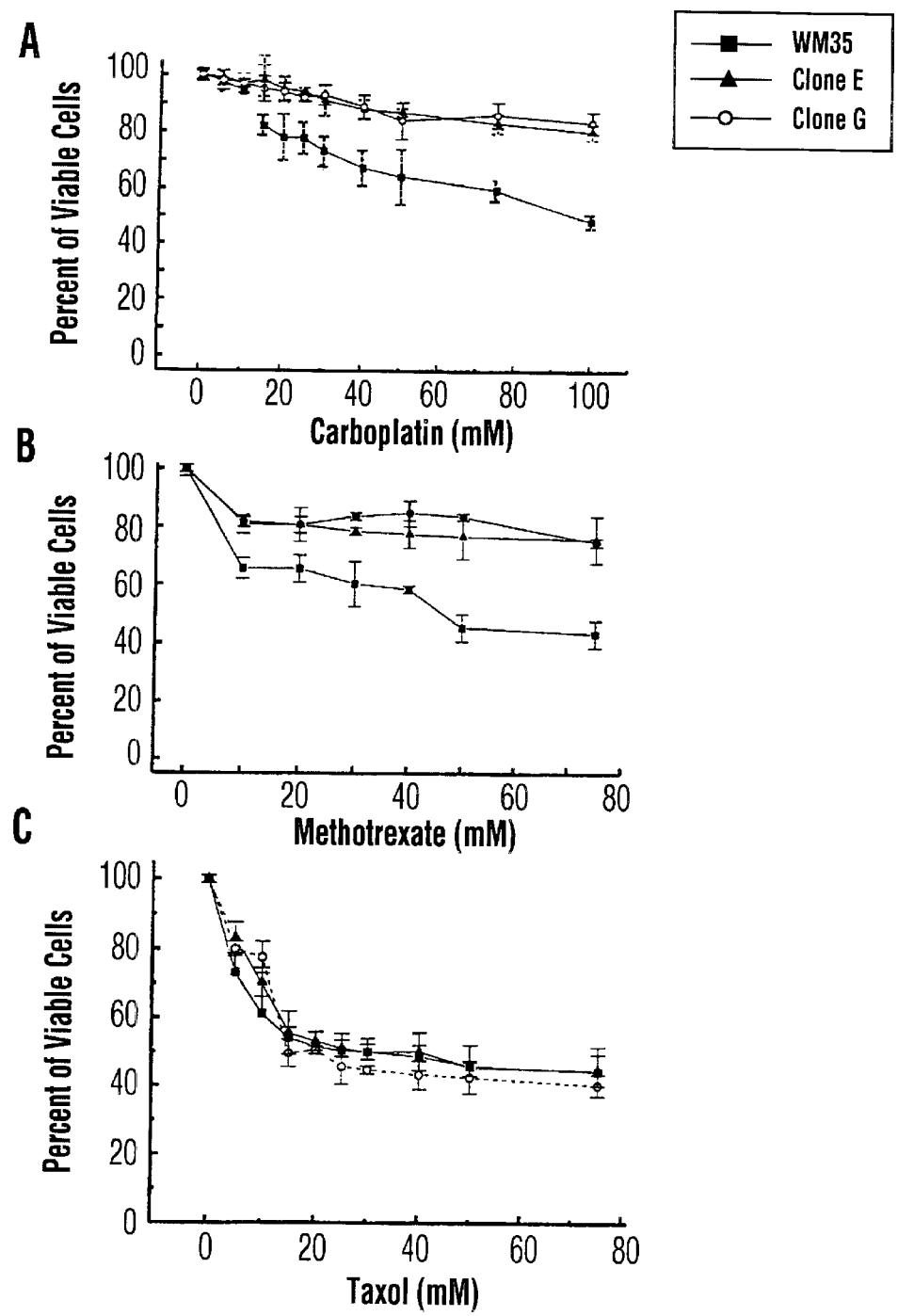
FIGS. 3A–3C illustrate cell viability after a 24 hour treatment of WM35, CDDP-resistant Clone E and CDDP-resistant Clone G cells with varying levels of either A) carboplatin, B) methotrexate, or C) taxol.

FIG. 3 illustrates cross resistance of the retrovirally derived drug resistant melanoma cell lines to various anti-cancer therapeutic drugs. The indicated cell lines were cultured in 96 well plates at a density of $8 \times 10^3$ cells per well and treated for 24 hours with either A) carboplatin; B) taxol; or C) methotrexate, at the indicated concentrations. Cell viabilities were determined using the MTS assay (Promega), measuring the cellular conversion of the tetrazolium salt, MTS, into formula which can be quantified at 490 nm. These results showed that Clone E and Clone G were more resistant to the cytotoxic effects of carboplatin and methotrexate, compared to WM35 cells. However, all three cell lines were equally sensitive to taxol treatment.

FIG. 3 illustrates that both Clone E and Clone G exhibited increased resistance to A) carboplatin and B) methotrexate compared to WM35 cells. However, these clones were equally sensitive to the cytotoxic effects of C) taxol as WM35. Thus, the CDDP-resistant clones were found to be cross-resistant to carboplatin and methotrexate but not to taxol.

Example 4

Analysis of the CRL-1 Proviral Integration Site

In order to investigate the mechanism of CDDP-resistance in the virally-derived clones, an attempt was made to identify the gene(s) having altered expression by proviral integration at CRL-1. Using host genomic sequences flanking the CRL-1 locus as probes for Northern blot analysis, a 3.5–4.0 kb transcript was detected which was significantly up-regulated in Clone E and Clone G compared to WM35. Analysis of approximately 10 kb of genomic sequence flanking the CRL-1 locus faed to identify any transcriptional domains. These results were not unusual since proviral integration has previously been shown to influence the expression of genes as far away as 90 kb from their site of integration (Bartholomew et al. (1991) *Mol. Cell. Biol.* 11:1820–1828). Consequently, in an attempt to identify this "CDDP-resistance gene" an alternative approach was used, in which total gene expression between Clone E and WM35 were compared by subtractive hybridization.

Example 5

Identiflcaton of TYRP2 as a Mediator of CDDP-Resistance

Subtractive hybridization is a widely utilized technique to isolate and identify genes that are differentially expressed in two distinct populations of cells. Using this approach, over 90 clones were isolated that were differentially expressed in Clone E cells compared to WM35 cells.

Figure 4:
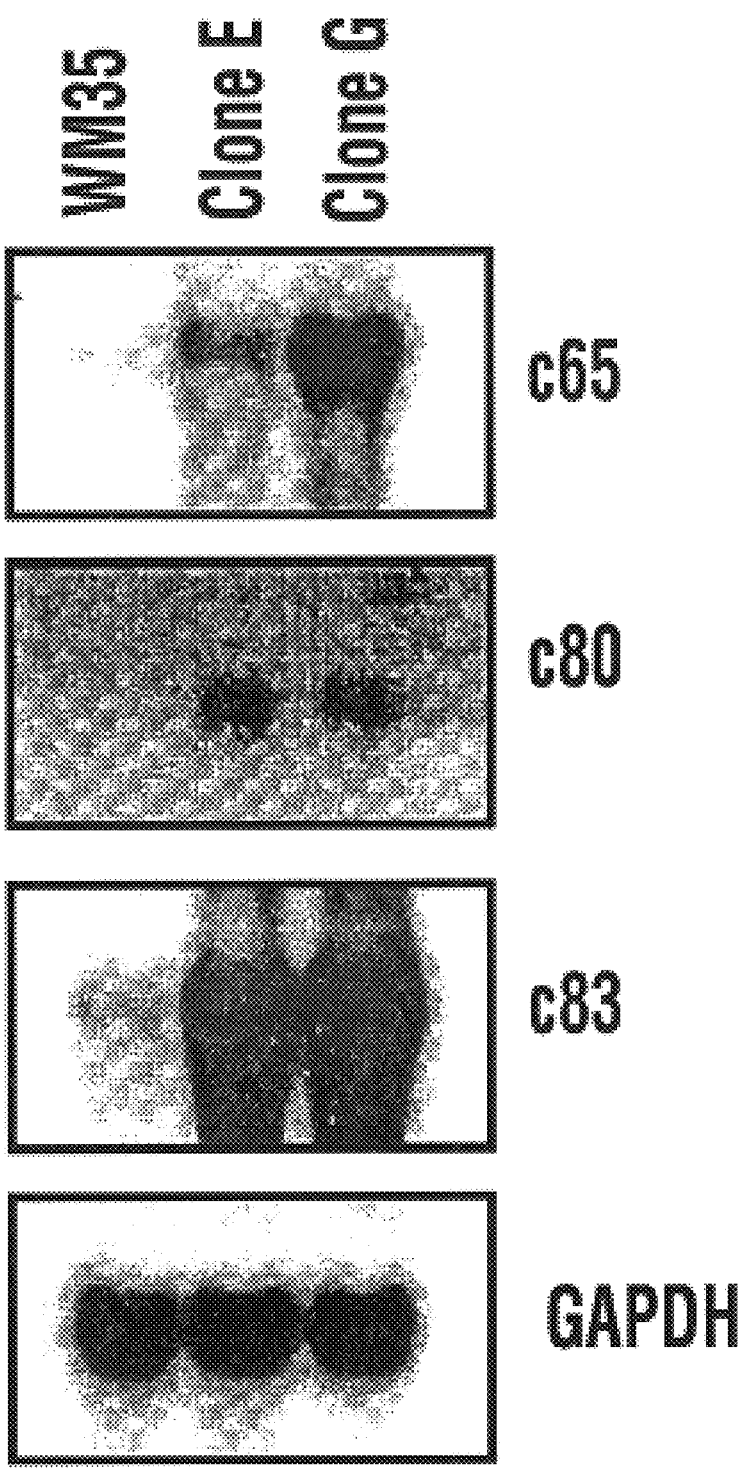
FIG. 4 shows a Northern blot analysis of differential gene expression between WM35, CDDP-resistant Clone E and CDDP-resistant Clone G cells.

FIG. 4 shows the results of subtractive hybridization analysis of the virally-derived Clone E cells and the parental WM35 cell line. Of nearly 100 clones isolated, only 3 (Clone 65; Clone 80; Clone 83) were confirmed to be differentially expressed by Northern blot analysis. DNA sequencing revealed that Clone 80 represented portions of the MSCV retrovirus used for infection. However, Clone 65 and Clone 83 were both 100% homologous to the 3' terminal end of tyrosinase-related protein 2 (TYRP2).

FIG. 4 illustrates a Northern blot analysis revealing that among the isolated clones, only three clones (Clone 65, Clone 80 and Clone 83) were in fact differentially expressed while the others represented false positive results. It was also determined that Clone 65, Clone 80 and Clone 83 were each expressed at higher levels in Clone E and Clone G relative to WM35.

Sequence analysis of these clones revealed that c80 was homologous to a portion of the MSCV retrovirus employed in the initial infecton. However, both c65 and c83 were 100% homologous to the 3'-untranslated region of the melanocyte-specific tyrosinase-related protein-2 (TYRP2) mRNA. TYRP2 and its protein product have previously been shown to function, in conjunction with tyrosinase and tyrosinase-related protein-1 (TYRP1), as enzymes that catalyze the conversion of L-tyrosine to the pigment melanin in melanocytes TYRP2 specifically catalyzes the conversion of L-DOPAChrome to 5,6-dihydroxyindole-2-carboxylic acid (DHICA) (Kameyama et al. (1993) *J. Invest. Dermatol.* 100:126–131).

Figure 5:
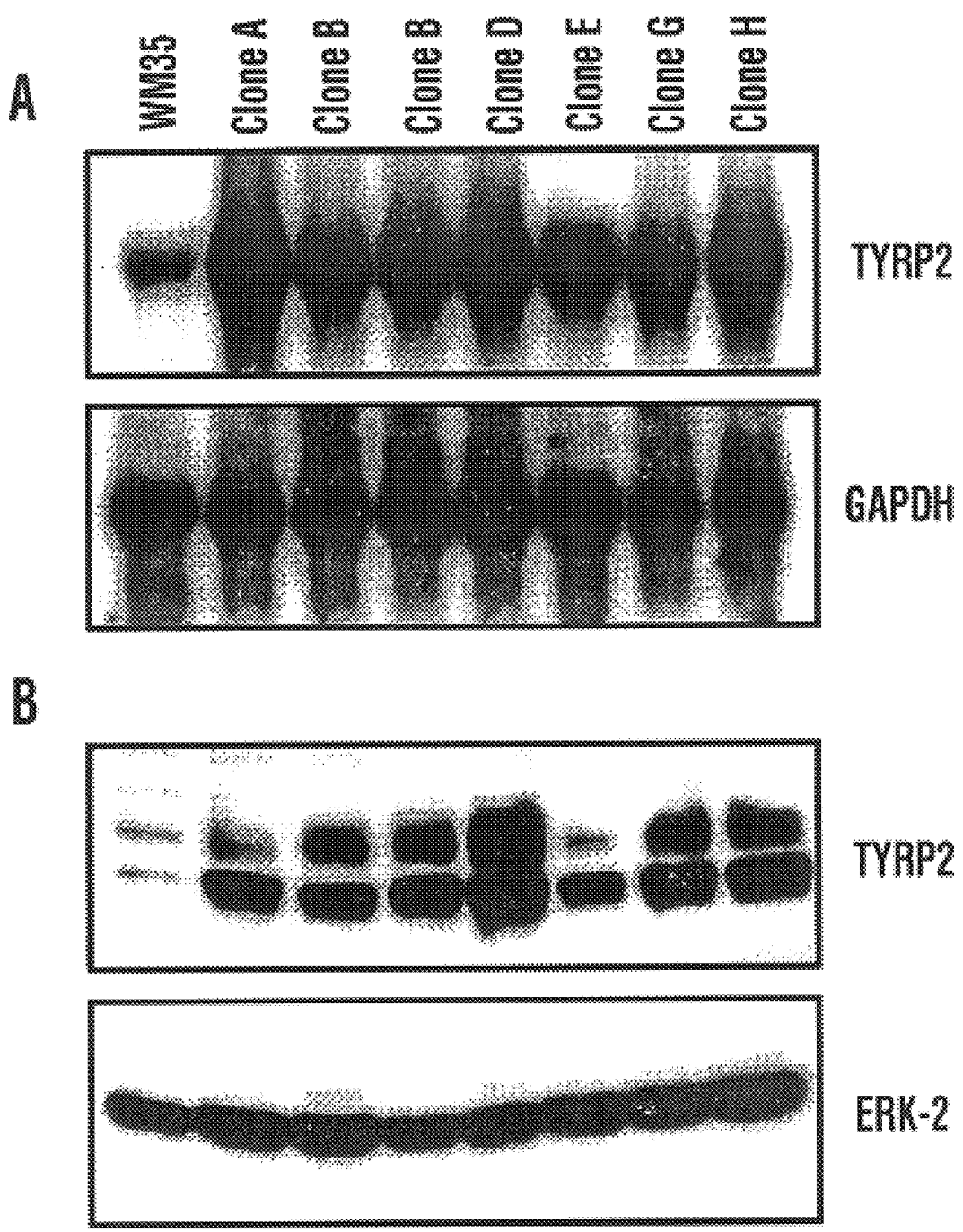
FIG. 5A shows a Northern blot analysis of TYRP2 cDNA in various cell types using a $^{32}$P-labelled TYRP2 cDNA probe, along with GAPDH mRNA as a control.
FIG. 5B shows a Western blot analysis of TYRP2 in various cell types visualized using immunoblotting with a polyclonal anti-TYRP2 antibody, along with ERK-2 as a control.

FIG. 5 illustrates the expression of TYRP2 in the virally-derived CDDP resistant clones by way of Northern blot analysis. For Northern analysis, 20 µg of total RNA was hybridized with a $^{32}$P-labelled TYRP2 cDNA probe. The level of GAPDH RNA was measured to assess the uniformity of RNA loading. This analysis showed that TYRP2 expression at the mRNA level was elevated in each of the virally-derived CDDP resistant clones relative to WM35 cells. Each of the virally-derived CDDP-resistant clones expressed higher levels of TYRP2 compared to WM35.

Figure 6:
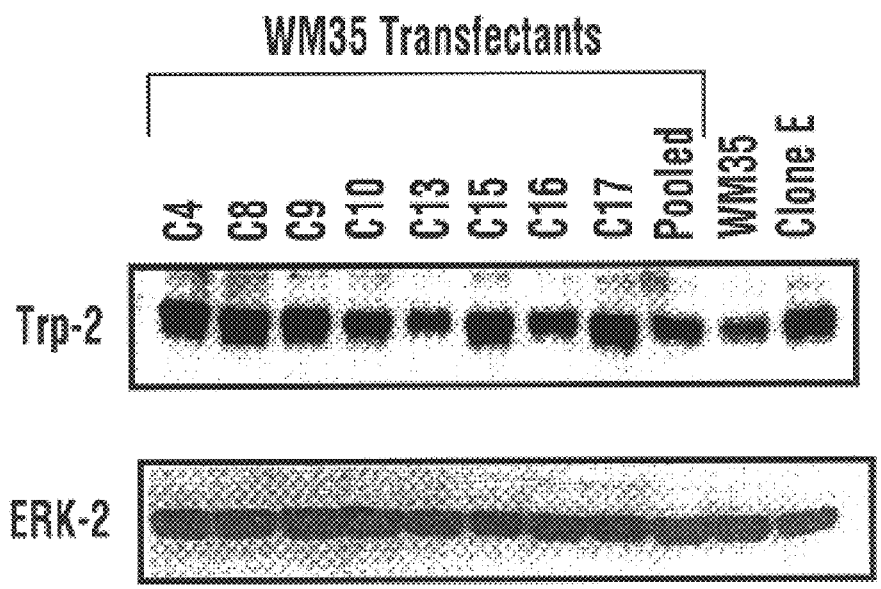
FIG. 6 shows a Western blot analysis of TYRP2 in WM35 cells transfected with a 2.1 kb TYRP2 fragment, vector alone transfected WM35 cells, and CDDP-resistant Clone E cells, along with ERK-2 as a control.

FIG. 6 illustrates the expression of TYRP2 in the virally-derived CDDP resistant clones via Western Blot analysis. For Western analysis, 15 µg of protein was resolved by SDS-polyacrylamide gel eletrophoresis and immunoblotted using a polyclonal antibody against TYRP2. The levels ERK-2 were measured to assess the uniformity of protein loading. This analysis shows that TYRP2 expression at the protein level was elevated in each of the virally-derived CDDP resistant clones relative to WM35 cells, consistent with the above observation that mRNA levels were elevated.

Example 6

Enforced Expression of TYRP2 in WM35 Cells Increased their Resistance to CDDP

To determine if TYRP2 expression alone can confer increased CDDP resistance, TYRP2 was cloned into a pcDNA3 expression vector (Invitrogen) and transfected into WM35 cells.

Figure 7:
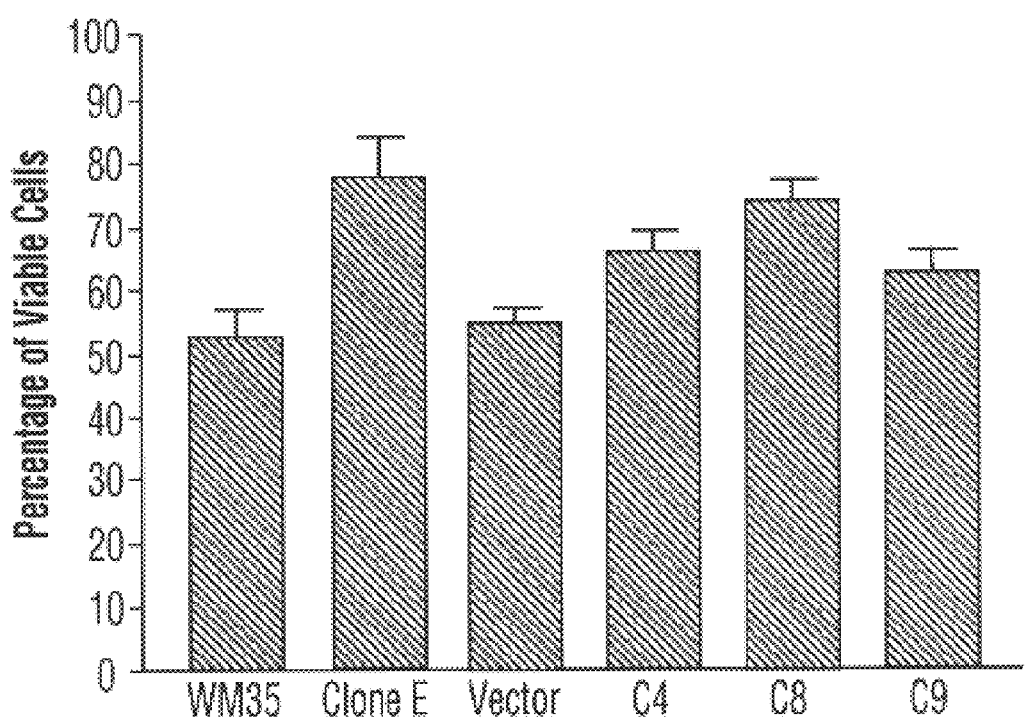
FIG. 7 shows cell viability after 24 hours of CDDP treatment for C4, C8 and C9 transfected cells which expressed high TYRP2 levels according to the Western blot analysis of FIG. 6, along with non-transfected WM35 cells, and CDDP-resistant Clone E cells.

FIG. 7 illustrates that transfection of TYRP2 into WM35 cells renders the cells more resistant to CDDP. A 2.1 kb fragment of TYRP2, which included the entire open reading frame, was cloned into the pcDNA3 expression vector and used to transfect WM35 cells. A) Proteins isolated from each transfectant were resolved by SDS-polyacrylamide gel electrophoresis and subjected to Western blot analysis using polyclonal anti-TYRP2 antibody. TYRP2 protein levels were elevated in each tnansfectant examined relative to WM35 parental cells. B) High TYRP2 expressing transfectants (c4, c8 and c9) were plated in 96-well plates at a density of $8 \times 10^3$ cells per well and treated with 15 µM of CDDP for 24 hours. Each transfectant demonstrated an increased level of resistance to CDDP relative to WM35 cells as determined by the MTS assay.

FIG. 7 illustrates that TYRP2 transfectants expressed higher levels of TYRP2 protein and were more resistant to CDDP (15 µM, 24 hours) than the parental WM35 cells, and that TYRP2 overexpression can confer increased resistance to CDDP in human melanoma cells.

Example 7

Levels of TYRP2 Expression Correlates with CDDP-Resistance in Human Melanoma Cell Lines In order to determine the scope of TYRP2-mediated CDDP-resistaace, 6 additional human melanoma cell lines were analysed for their levels of TYRP2 expression and relative sensitivities to CDDP.

Figure 8:
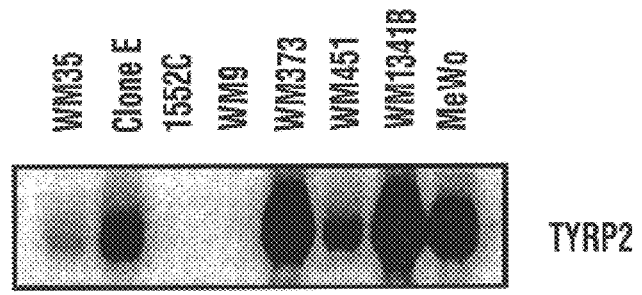
FIG. 8 illustrates TYRP1 mRNA expression in different melanoma cell lines, as well as in WM35 cells, and CDDP-resistant Clone E cells, determined by Northern blot analysis.

FIG. 8 illustrates TYRP2 expression in a panel of melanoma cell lines. The constitutive levels of TYRP2 mRNA expression in 6 different melanoma cell lines in addition to WM35 and Clone E cells, were determined by Northern blot analysis. The levels of TYRP2 expression were shown to be variable with WM373, WM451, WM1341B and MeWo expressing higher levels than WM35 cells. The cell tines 1552C and WM9 expressed little to undetectable levels of TYRP2.

Figure 9:
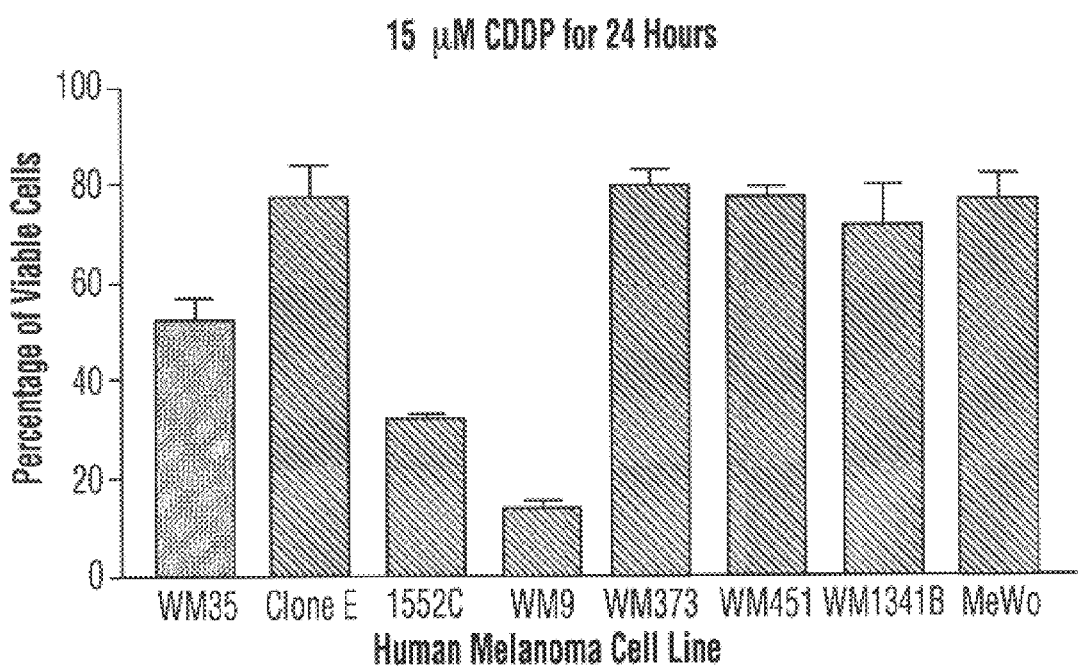
FIG. 9 shows cell viability after 24 hours of CDDP treatment for different melanoma cell lines, along with WM35 cells, and CDDP-resistant Clone E cells.

FIG. 9 illustrates the response of melanoma cell lines to CDDP treatment. Each of the cell lines indicated were plated in 96-well plates at a density of $1 \times 10^5$ cells/well and treated with 15 µM CDDP for 24 hours. Percentage of viable cells were determined by the MTS assay. Cell lines that expressed high levels of TYRP2 (ie: Clone E, WM373, WM451, WM1341B, MeWo) showed substantially higher survival compared to WM35 cells. WM9 and 1552C cells, which express very low levels of TYRP2 were highly sensitive to CDDP treatment. The levels TYRP2 expression in these cells directly correlated with their resistance to CDDP treatment (15 µM CDDP, 24 hours). For example, the cell line WM9, which expresses very low levels of TYRP2 was very sensitive to CDDP treatment (<20% of cells survived). Conversely, the cell lines WM451 and MeWo, for example, which express high levels of TYRP2 were resistant to CDDP treatment (approximately 80% of cells survived). Thus, these results indicate that TYRP2-mediated CDDP resistance is not cell line specific, but may be generally applicable to human melanoma cells.

Example 8

TYRP2 Mediated CDDP Resistance is Independent of TYRP1 Expression and Melanin Content The pigment melanin has previously been shown to have protective effects on cells. It is widely known that the light absorption property of melanin serves to protect the skin from UV(B) radiation. Melanin is also a powerful cation chelator, has been postulated to act as a free radical sink (Riley (1997) *Int. J. Biochem. Cell Biol.* 29:1235–1239), and has been implicated in the protection of melanocytes from various compounds.

Figure 10:
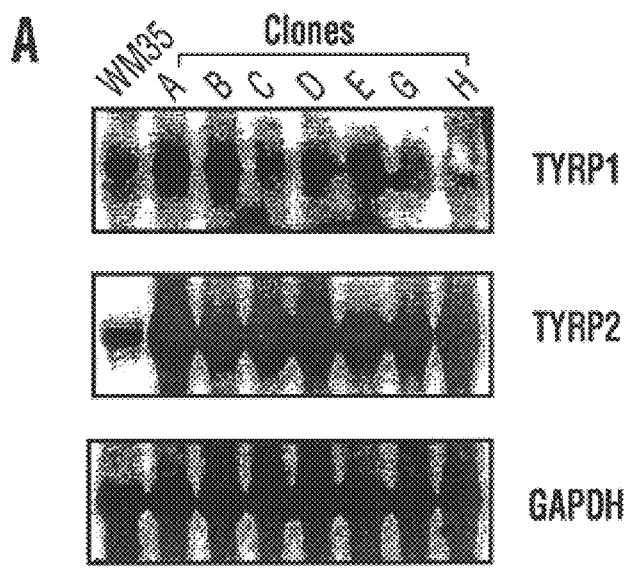
FIG. 10 shows a Northern blot analysis of TYRP1 and TYRP2 expression for WM35 cells and a variety of CDDP-resistant clones, along with GAPDH expression as a control.

FIG. 10 illustrates the analysis of TYRP1 expression in the virally-derived clones by Northern blotting showed no correlation with the expression of TYRP2. These data show that TYRP1 expression in each of the virally-derived CDDP resistant clones showed no correlation with CDDP resistance nor with the expression of TYRP2.

Figure 11:
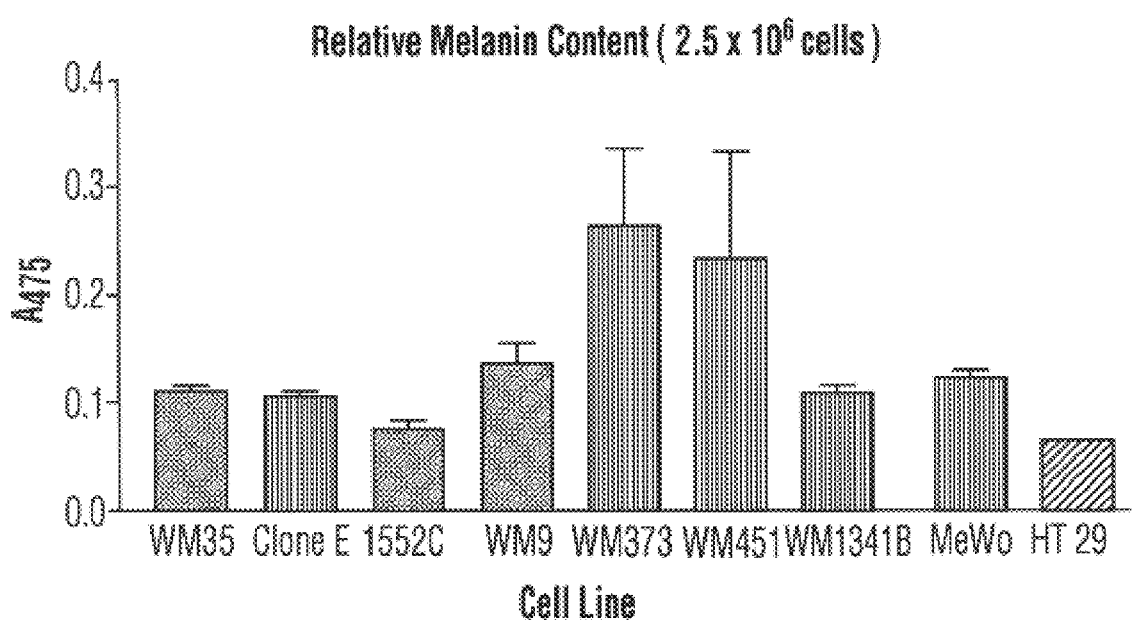
FIG. 11 illustrates relative melanin content in human melanoma cell lines.

FIG. 11 illustrates relative melanin content as determined by vigorously vortexing $2.5 \times 10^6$ cells in 1 N NaOH, followed by spectrophotometric analysis at 475 nm. The melanin contents of a panel of human melanoma cell lines did not correlate with CDDP resistance nor with TYRP2 expression. These results indicate that TYRP2-mediated CDDP resistance is independent of melanin content and other enzymes of the melanin biosynthetic pathway. Further, the melanin content in the panel of melanoma cell lines tested did not correlate with the levels of TYRP2, as determined above in Example 7 and illustrated in FIG. 8.

Example 9

Correlation Between TYRP2 Expression and CDDP Resistane in vivo

In order to determine the significance of TYRP2-mediated CDDP resistance in vivo, tumors were generated in immunodeficient CD-1 mice by subcutaneous injection of $2 \times 10^6$ cells of either MeWo or WM9. WM35 cells were not used for in vivo studies because they lack tumorigenicity (Bani et al. (1996) *Cancer Res.* 56:3075–3086). MeWo is a human melanoma cell line that has been shown to express high levels of TYRP2 and is resistant to CDDP in vitro, while WM9 cells express very low levels of TYRP2 and are sensitive to CDDP treatment. Mice bearing these tumors were treated with CDDP three times weekly at a dose of 2 mg/kg.

Figure 12:
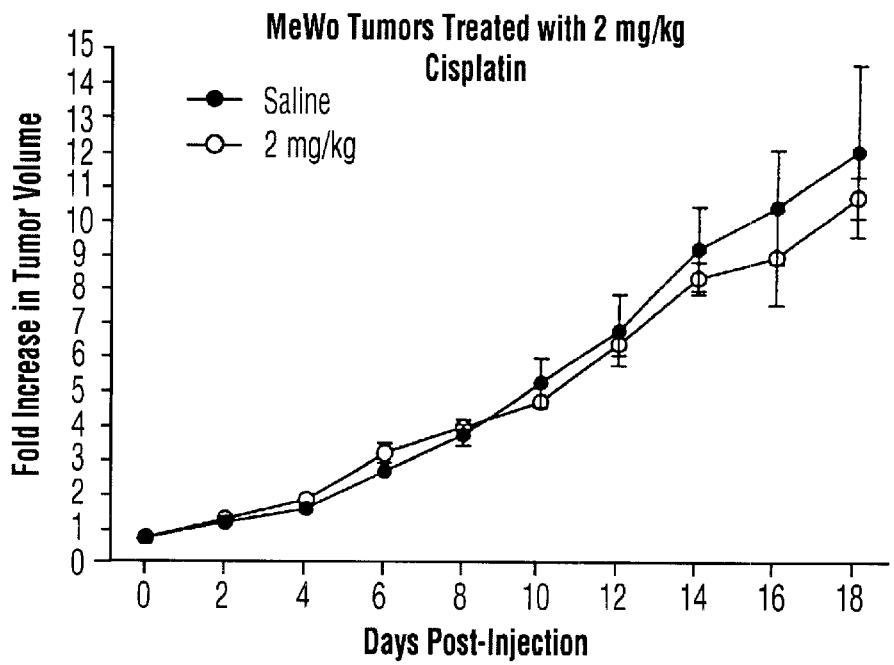
FIG. 12 illustrates changes in MeWo tumor volume over time in mice injected with either CDDP or a saline control

FIG. 12 illustrates the correlation between TYRP2 expression and CDDP resistance in vivo. Tumors were generated in immunodeficient CD-1 nude mice by subdermally injecting MeWo cells. The growth rates of tumors generated with MeWo cells did not differ between CDDP treated mice (2 mg/kg/2 days–maximum tolerated dose) and saline treated mice. MeWo derived tumors did not respond to CDDP treatment relative to saline injected controls.

Figure 13:
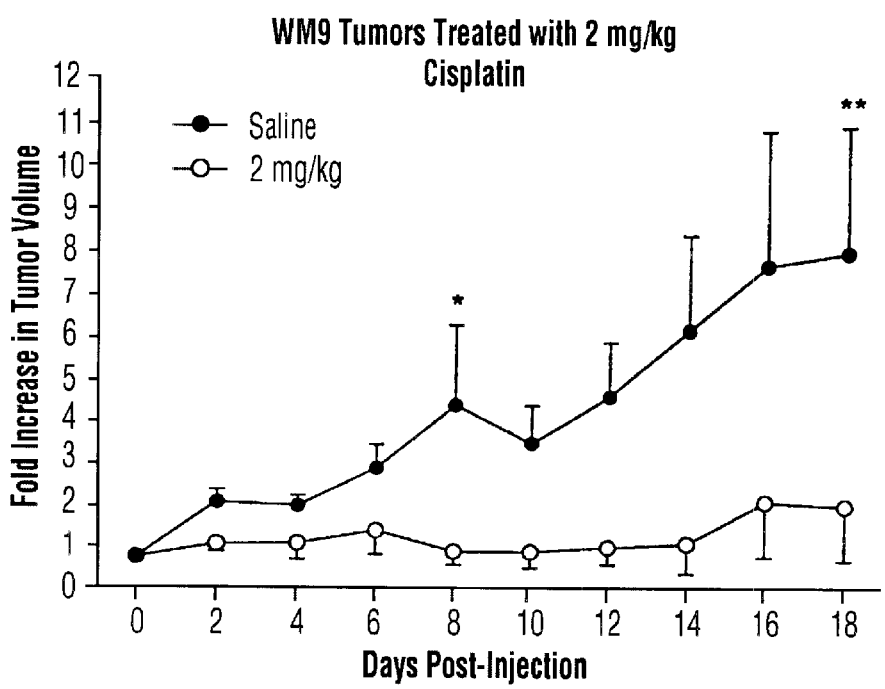
FIG. 13 illustrates changes WM9 tumor volume over time in mice injected with either CDDP or a saline control.

FIG. 13 illustrates the correlation between TYRP2 expression and CDDP resistance in vivo in WM9 cells. Tumors were generated in immunodeficient CD-1 nude mice by subdermally injecting WM9 cells. Tumors generated with WM9 cells showed a significant reduction in growth rates during CDDP treatment at the same dose relative to saline treated controls. By day 18 of treatment, the tumors in 2 of 5 mice had completely disappeared. Thus, these results indicate that the correlation between TYRP2 expression and CDDP resistance is applicable to melanoma tumors generated in vivo.

It was previously shown that MeWo cells express high levels of TYRP2 and were resistant to CDDP in vitro, whereas WM9 cells were shown to express very low levels of TYRP2 and were sensitive to CDDP in vitro.

Example 10

Method of Determining Cross-Resistance to Other Anti-Cancer Therapeutic Drugs

The determination of cross resistance of CDDP-resistant cells to other anti-cancer therapeutic agents is accomplished by a comprehensive screening of a large number of anti-cancer therapeutic agents to determine if cytotoxic effects of the agents on melanoma cells correlate with TYRP2 expression. Dose-response experiments are performed using several melanoma cell lines that express either high (WM373, WM451, WM1341B, MeWo) or low (WM35, WM9, 1552C) levels of TYRP2. After plating these cells in 96-well plates at a density of 10,000 cells per well, attached cells are treated with various doses of anti-cancer therapeutic agents for 24 hours and the percentage of surviving cells is determined by the MTS assay (Promega). This analysis provides the $LD_{50}$ of each drug for comparison to the relative levels of TYRP2 in each cell line, to determine the correlation of cytotoxic effects with TYRP2 level.

Example 11

Manipulation of TYRP2 Expression and CDDP Response

The constitutive levels of TYRP2 expression corelates with CDDP resistance in melanoma cells both in vitro and in vivo. It has been demonstrated that the enforced expression of TYRP2 in WM35 cells by transfection rendered WM35 more resistant to CDDP, suggesting that the manipulation of TYRP2 expression in melanoma cells can modulate their resistance to CDDP.

In order to demonstrate that the increased resistance of WM35 cells to CDDP following TYRP2 transfection is not a cell type specific phenomenon, two other human melanoma cell lines, WM9 and 1552C are similarly transfected with TYRP2. WM9 and 1552C have previously been shown to express very low levels of TYRP2 and to be highly sensitive to CDDP. Transfections and CDDP dose-response experiments are performed as described above.

TYRP2 levels in melanoma cell lines that highly express TYRP2 are decreased by antisense strategies. For example, the cell lines WM373, WM451, WM1341B and MeWo are utilized since they have previously been shown to constitutively express high levels of TYRP2 and to be highly resistant to CDDP. Two distinct approaches are utilized to administer TYRP2 antisense oligonucleotides. First, several phosphorothioated antisense oligonucleotides targeting the ATG translation initiation codon and various regions of the TYRP2 mRNA are designed as well as their respective mismatched controls. Antisense oligonucleotides are administered to cultured cells by Lipofectamine (Life Technologies) according to the manufacturer's instructions. Those oligonucleotides found to effectively down-regulate TYRP2 expression are used for subsequent in vivo studies.

The 2.1 kb TYRP2 cDNA fragment, provided by Dr. Rick Sturmas described above, is cloned into the pcDNA3 expression vector (Invitrogen) in the antisense orientation and used for transfection. Cells exhibiting a down-regulation in TYRP2 protein expression by either method of antisense administration are analyzed for their response to various doses of CDDP and compared to the response of their respective wild-type cells.

Example 12

CDDP Response of Tumors Generated with TYRP2 Sense and Antisense Transfectants

It has been demonstrated that the correlation between TYRP2 expression and CDDP resistance also applies in vivo. In the studies outlined above, it was shown that tumors generated in immunodeficient CD-1 mice with MeWo cells (high levels of TYRP2; CDDP resistant in vitro; FIG. 12) and WM9 cells (low levels of TYRP2; CDDP sensitive in vitro; FIG. 13) were unresponsive and responsive to CDDP treatment, respectively, at a dosage of 2 mg/kg/2 day i.p.

Similar experiments are conducted using 1552C (low levels of TYRP2; CDDP sensitive) and WM451 (high levels of TYRP2; CDDP resistant) cells, both of which have previously been shown to be tumorigenic. These studies are repeated using tumors generated with WM9 and 1552C TYRP2 transfectants and MeWo and WM451 TYRP2 antisense transfectants. TYRP2 transfection into WM9 and 1552C cells renders these tumors more resistant to CDDP. Conversely, tumors generated with MeWo and WM451 TYRP2 antisense transfectants exhibit increased sensitivity to CDDP compared to tumors generated with the parental cell lines.

Example 13

Chemosensitization of CDDP Resistant Melanoma Tumors by TYRP2 Antisense Oligonucleotide Therapy In order to develop an in vivo approach to chemosensitize CDDP resistant melanoma tumors, TYRP2 antisense oligonucleotide therapy is utilized. This approach has previously been shown to be effective in the targeting of various mRNA both in vitro and in vivo (Webb et al. (1997) *Lancet* 349:1137–1141; Monia et al. (1996) *Nat. Med.* 2:668–675). Indeed, it was demonstrated by Jansen and colleagues (Jansen et al. (1998) *Nat. Med.* 4:232–234) that antisense oligonucleotide therapy directed against Bcl-2 effectively down-regulated Bcl-2 protein expression in human melanoma tumors grown in SCID mice and significantly increased their sensitivity to dacarbazine. Using the TYRP2 antisense phosphorothioate oligonucleotides that effectively down-regulated TYRP2 protein expression in section 2 above, TYRP2 is down-regulated in MeWo and WM451 xenotransplanted tumors. Tumors are generated by injecting 2.0×10$^6$ cells subdermally into the lower left flanks of immunodeficient CD-1 mice. An antisense phophorothioate oligonucleotide, a mismatched oligonucleotide control or saline is administered using constant infusion miniosmotic pumps (Alzet 2002, Alzet) at an infusion rate of 5 mg/kg per day. Concurrently, the mice are treated with either saline or CDDP (2 mg/kg/2 days i.p.). The animal weights and tumor volume are measured daily.

Example 14

CRL-1 Gene Identification

As described previously, many of the virally-derived CDDP resistant clones obtained by retroviral insertional muatagenesis had acquired the integration of a single provirus at the CRL-1 locus. Although the chromosomal location of the CRL-1 locus (Human Chromosome 3) is distinct from that of TYRP2 (Human Chromosome 13q31–q32), it is reasonable to postulate that target gene(s) at the CRL-1 locus regulates the expression of TYRP2. Indeed, each CDDP resistant clone that had acquired CRL-1 rearrangement showed a significant increase in TYRP2 expression. Thus, the identification of this gene(s) provides important insights into the regulation of TYRP2.

In order to clone the CRL-1 gene, the CRL-1 integration site is isolated and its genomic junctional sequences determined by screening a human BAC genomic library. Transcriptional domains located within BAC clones that contain between 100–150 kb of the CPL-1 are located by exon trapping (Life Technologies). Once obtained, these sequences(s) are compared to existing sequences in GenBank in order to determine their identity. The cDNA and genomic libraries are then screened to determine the full mRNA and genomic sequences of this gene. Using cDNA expression vectors of this CRL-1 target gene, WM9, WM35 and 1552C cells are transfected using Lipofectamine (Life Technologies) and its subsequent effects on TYRP2 expression and CDDP resistance is determined by Northern and Western blot analysis, and by CDDP dose-response studies.

Example 15

Radiation Resistant Cells

Gamma radiation resistant mutant cell lines were selected using retroviral insertional mutagenesis, with selection based on resistance to gamma radition. X-ray resistant mutant cell lines, designated as "XR" were established.

Figure 14:
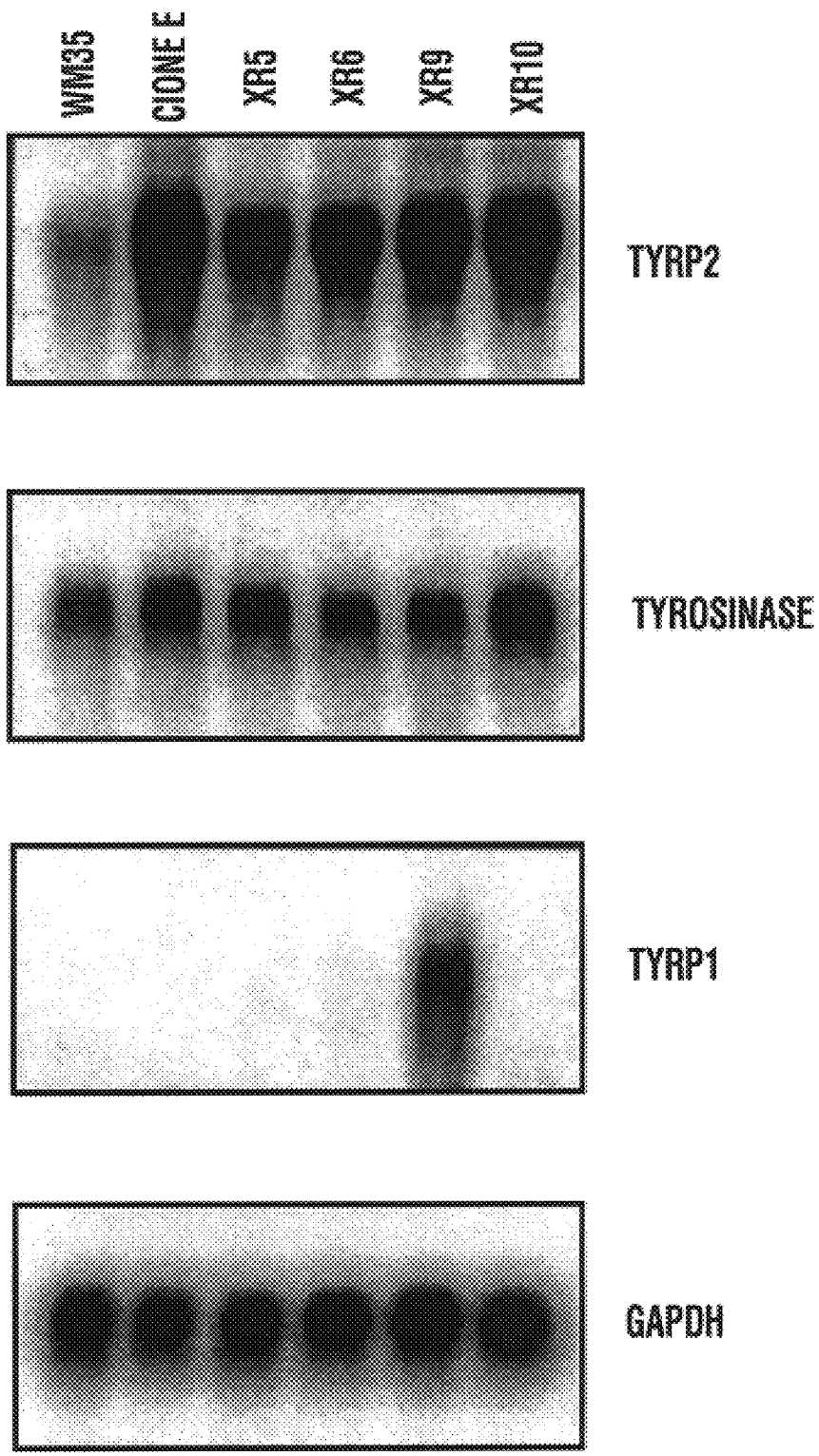
FIG. 14 shows a Northern blot analysis of TYRP2, tyrosinase, and TRP-1 expression in WM35 cells, CDDP-resistant Clone E cells, and radiation-resistant variants generated by retroviral insertion mutagenesis, along with GAPDH expression as a control.

FIG. 14 shows a Northern blot analysis of expression of three melanogenic enzymes, namely: TYRP2, tyrosinase, and TYRP1 in WM35 cells, Clone E cells, and in x-ray resistant cell lines designated as XR5, XR6, XR9 and XR10. Hybridization with a GADPH probe was used as a control to demonstrate uniformity of RNA loading. Of the three melanogenic enzymes, only the expression of the mRNA encoding TYRP2 was consistently elevated in each of the x-ray resistant mutants, relative to the WM35 cells.

Figure 15:
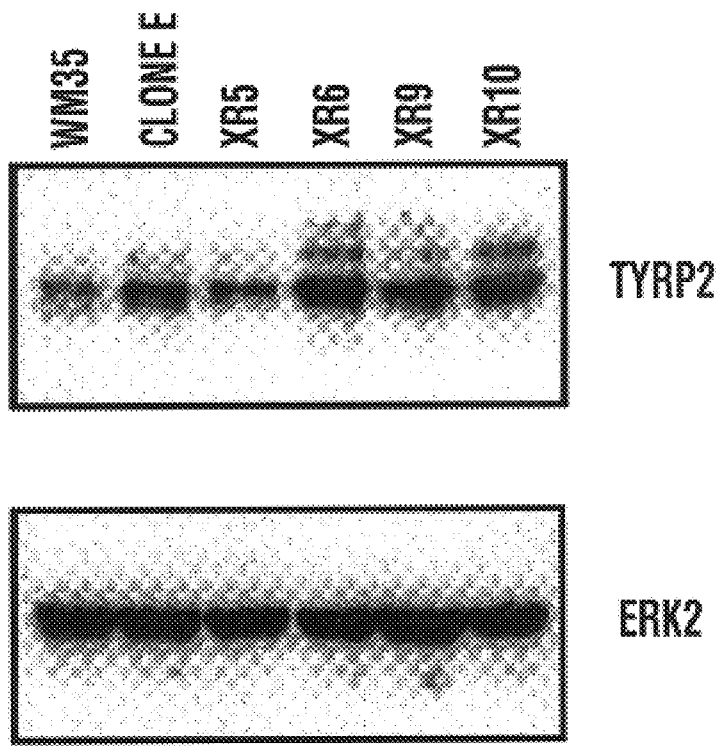
FIG. 15 shows a Western blot analysis of TYRP2 protein expressed in WM35 cells, CDDP-resistant Clone E cells, and radiation-resistant variants generated by retroviral insertion mutagenesis, using ERK-2 as a control.

FIG. 15 shows a Western blot analysis of TYRP2 protein expression in WM35 cells, Clone E cells, and in x-ray resistant cell lines designated as XR5, XR6, XR9 and XR10. Protein extracts were resolved by SDS-PAGE, transferred to PVDF membranes and incubated with the α-PEP8 anti-TYRP2 antibody. Levels of ERK2 were determined as a control to demonstrate uniformity of protein loading. TYRP2 protein levels were significantly elevated in Clone E, and in the x-ray resistant cell lines relative to WM35, consistent with the levels of mRNA expressed in the cells, as illustrated in FIG. 14.

Example 16

Correlation of TYRP2 Expression with Resistance to CDDP and UV(B)

An assessment was performed to determine whether TYRP2 expression in melanoma cell lines is predictive of susceptibility to either or both CDDP and TV(B) treatements.

Figure 16:
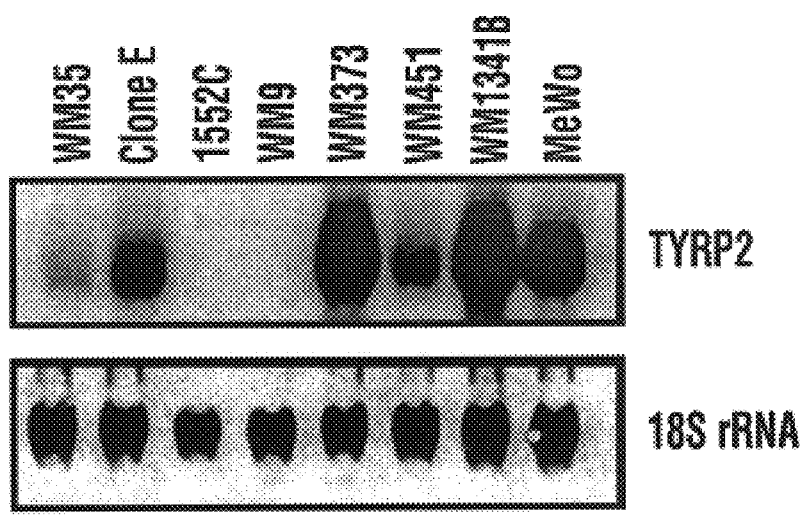
FIG. 16 illustrates a Northern blot analysis of TYRP2 expression levels in WM35 cells, CDDP-resistant Clone E cells, and other human melanoma cell lines, using 18S rRNA as a control.

FIG. 16 illustrates a Northern blot analysis of TYRP2 mRNA levels in a panel of human melanoma cell lines. The WM35 cell line, the CDDP-resistant Clone E and various representative cell lines which express low and high levels of TYRP2 were assessed. The level of 18S rRNA was used as a control to ensure uniform loading of RNA.

Those cells exhibiting high or low TYRP2 expression according to the results of the Northern blot of FIG. 16 were selected for further analysis in a UV(B) survival assay. The UV(B) survival assay is conducted by exposing cells to UV(B) irradiation at a level of 5 mJ/cm$^2$. The percentage of surviving cells is determined after 24 hours of exposure.

Table 2 provides the results of the UV(B) survival assay. Those cells expressing high levels of resistance to UV(B) irradiation (Clone E, MeWo and XR9) demonstrated a significantly higher level of resistance to UV(B) irradiation relative to cells that express low levels of TYRP2 (WM35 and WM9).

TABLE 2

UV(B) Susceptibility and TYRP2
Expression of Melanoma Cell Lines

| Cell Line | TYRP2 Expression | n | % Survival* |
|---|---|---|---|
| WM35 | ++ | 3 | 38.7 ± 1.8 |
| Clone E | ++++++ | 3 | 67.3 ± 4.0 |
| WM9 |  | 3 | 16.7 ± 1.5 |
| MeWo | ++++++++ | 3 | 69.1 ± 5.2 |
| XR9 | +++++ | 3 | 61.2 ± 2.6 |

*Values shown are means ± SEM.

To determine the correlation between levels of TYRP2 expression and CDDP resistance, the cells assessed in the UV(B) survival assay as shown in Table 2 were further assessed for resistance to CDDP. Cells were plated in 96-well plates and treated with 15 μM CDDP. After a 24 hour incubation, cell viability was determined by the MTS assay.

Table 3 provides the result of the CDDP resistance assessment. Cells expressing high levels of TYRP2 (Clone E, MeWo and XR9) were more resistant to CDDP treatanent relative to cells that express low levels of TYRP2 (WM35 and WM9).

These data indicate a strong correlation between TYRP2 levels and UV(B) susceptibility, implicating TYRP2 level as a mediator of resistance to both CDDP treatment and resistance to radiation therapy. The targeting of TYRP2 thus provides a means of sensitizing resistant melanoma cells to these and other anti-cancer treatments involving anti-cancer therapeutic agents and/or ionizing radiation.

TABLE 3

TYRP2 Expression and CDDP-Resistance of
Melanoma Cell Lines

| Cell Line | TYRP2 Expression | n | % Survival* |
|---|---|---|---|
| WM35 | ++ | 3 | 52.6 ± 4.4 |
| Clone E | ++++++ | 3 | 77.4 ± 6.7 |
| WM9 |  | 3 | 13.8 ± 1.6 |
| MeWo | ++++++++ | 3 | 77.0 ± 5.3 |
| XR9 | +++++ | 3 | 82.4 ± 1.7 |

*Values shown are means ± SEM.

Example 17

Effect of UV(B) Radiation on Various Cell Lines

An assessment was performed to determine the effect of UV(B) irradiation on various cell types, including those transfected with TYRP2, and those known to be x-ray resistant.

The cells used were: (1) WM35 cells, x-ray resistant cell lines (2) XR9 and (3) XR10, (4) a CDDP-resistant (Clone E) variant generated by retroviral insertional mutagenesis, (5) a control WM35 cell transfected with a vector (without TYRP2), and (6) a WM35 TYRP2-transfectant line (C8). Cells were treated with 5 mJ/cm$^2$ UV(B) radiation. Cell viability at 24 hours following treatment was determined by trypan blue exclusion.

Figure 17:
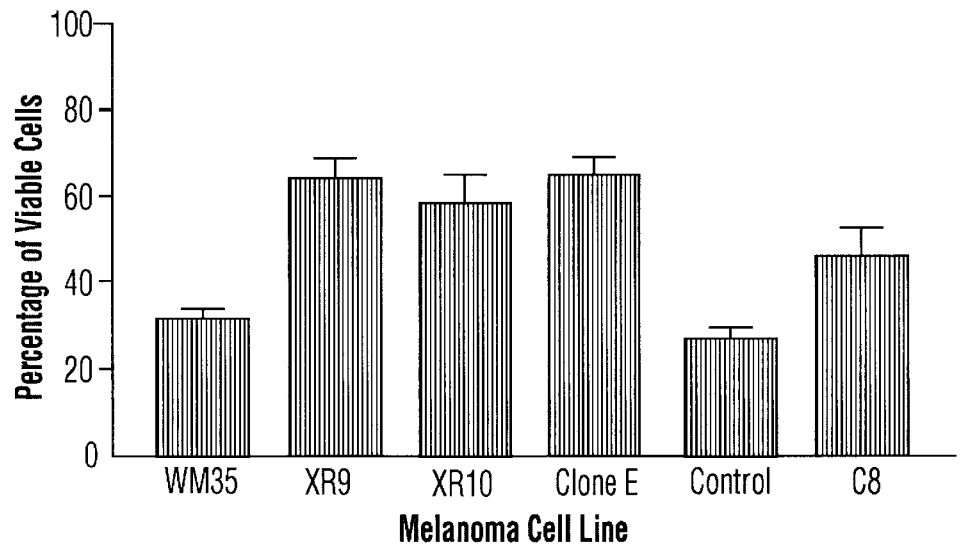
FIG. 17 illustrates the effect of UV(B) radiation on viability of WM35 cells, x-ray resistant cells (XR9, XR10), and CDDP-resistant variants generated by retroviral insertional matagenesis (Clone E), as well as WM35 TYRP2 transfectant cells (C8), and vector transfected control cells (Control).

FIG. 17 illustrates the results of this treatment protocol. The x-ray resistant cell lines, the CDDP resistant variant cells, and the WM35 TYRP2 transfectant line exhibit increased resistance to UV(B) irradiation relative to wild type WM35 cells and the control cells transfected with the vector alone. Thus, the TYRP2-transfectant cell line (C8) showed enhanced resistance to UV(B) radiotherapy, indicating that the presence of TYRP2 conferred anti-cancer therapy resistance to these cells. Clearly, lower levels of TYRP2 in the control cells rendered these cells more sensitive to radiotherapy.

Example 18

Effect of UV(B) Radiation on a Panel of Transformed Human Melanoma Cells

The following assessment was performed to determine the effect of UV(B) irradiation on various transformed human melanoma cells.

The cells used were: (1) WM35 cells, (2) WM9 cells (3) WM239 cells, (4) WM1341B cells, and (5) MeWo cells. Cells were treated with 5 mJ/cm$^2$ UV(B) radiation and viable cells at 24 hours following treatment were determined by trypan blue exclusion.

Figure 18:
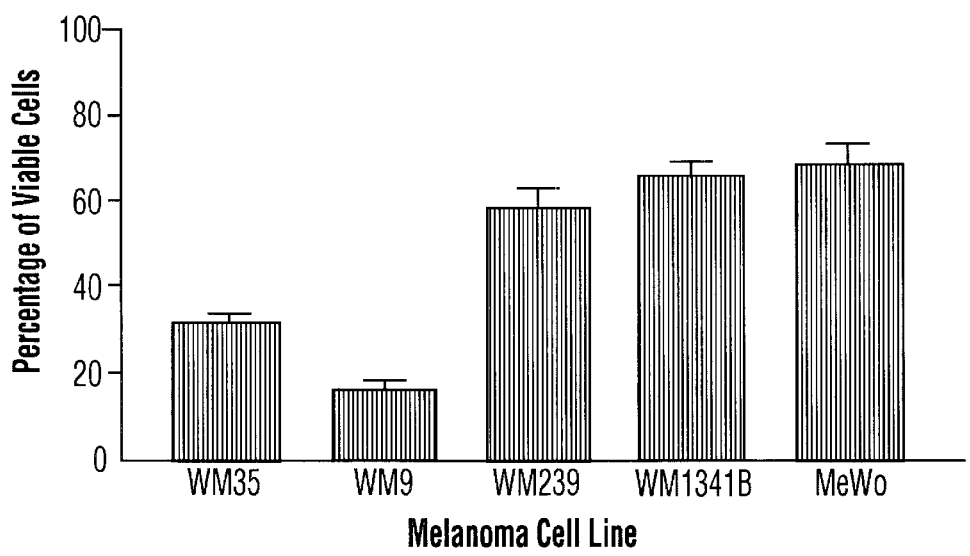
FIG. 18 illustrates UV(B) radiation resistance in a panel of human melanoma cells.

FIG. 18 illustrates the results of this treatment protocol. The results demonstrate that cell lines expressing low to undetectable levels of TYRP2 (WM35, WM9) are significantly more sensitive to UV(B) irradiation relative to high TYRP2 expressing cells (WM239, WM1341B, and MeWo). Thus, cellular TYRP2 levels were again found to be positively correlated with resistance anti-cancer treatment.

Example 19

Quantitative Evaluation of TYRP2 in a Biopsy Sample

A biopsy sample is obtained from a patient having melanoma. Using a polymerase chain reaction (PCR) technique, RNA is extracted from a biopsy sample. cDNA is synthesized from the RNA and using primers directed against TYRP2 are subsequently used to amplify the TYRP2 cDNA. Agarose gel electrophoresis is utilized to determine the quantity of TYRP2 cDNA which is proportional to the TYRP2 mRNA in the melanoma.

Internal standards run on the same gel are used to compare the relative intensity of the melanoma TYRP2 in the biopsy sample to determine the likely sensitivity of the biopsied melanoma to a particular anti-cancer therapeutic agent.

To compare the relative level of TYRP2 in the biopsy sample with a level indicative of anti-cancer therapy resistance, a range of TYRP2 cDNA is established and this value is compared with that of the biopsy sample.

REFERENCES

Altschul et al., (1990) *J. Mol. Biol.*, 215, 403–410.
Armstrong B K, Kricker A. (1994) *Cancer Surv.* 19–20:219–240.
Bani M R, Rak J, Adachi D, Wiltshire R, Trent J M, Kerbel R S, Ben-David Y. (1996) *Cancer Res.* 56:3075–3086.
Bartholomew C. Ihle J N. (1991) *Mol. Cell. Biol.* 11:1820–1828.
Bernal S D, Speak J A, Boeheim K, Dreyfiss A I, Wright J E, Teicher B A, Rosowsky A, Tsao S W, Wong Y C. (1990) *Mol. Cell. Biochem.* 95:61–67.
Bradley G, Juranaka P F, Ling V. (1988) *Biochim. Biophys. Acta* 948:87–128.
Gornati D, Zaffaroni N, Villa R, DeMarco C, Silverstrini R. (1997) *Anti-cancer Drugs* 8:509–516.
Jackson et al., (1992) *EMBO J.*, 11, 527–535.
Jansen B, Schlagbauer-Wadl H, Brown B D, Bryan R N, van Elsas A, Muller M, Wolff K, Eichler H G, Pehamberger H. (1998) *Nat. Med.* 4:232–234.

Kameyama K, Takemura T, Hamada Y, Sakai C, Kondoh S, Nishiyama S, Urabe K, Hearing V J. (1993) *J. Invest. Dermatol.* 100:126–131.

Kuroda H, Sugimoto T, Ueda K, Tsuchida S, Horii Y, Inazawa J, Sato K, Sawada T, (1991) *Int. J. Cancer* 47:732–737.

Laemmli, UK (1970) *Nature,* 227, 680–685.

Lorico A, Toffoli G, Bolocchi M, Erba E, Broggini M, Rappa G, D'Incalci M. (1988) *Cancer Res.* 48:2036–2041.

Lu S, Man S, Bani M R, Adachi D, Hawley R G, Kerbel R S, Ben-David Y. (1995) *Cancer Res.* 55:1139–1145.

Monia B P, Johnston J F, Geiger T, Muller M, Fabbro D. (1996) *Nat. Med.* 2:668–675.

Riley P A. (1997) *Int. J. Biochem. Cell Biol.* 29:1235–1239.

Sambrooke et al., (1989). Molecular Cloning: A Laboratory Manual, 2nd edition. Cold Spring Laboratory Press: Cold Spring Harbour.

Webb A, Cunningham D, Cotter F, Clarke P A, di Stefano F, Ross P, Corbo M, Dziewanowska Z. (1997) *Lancet* 349:1137–1141.

All documents and references noted or discussed above are herein incorporated by reference in their entirety. The aboveescribed embodiments and examples of the invention are intended to be illustrative of the present invention. Alterations, modifications and variations may be effected the particular embodiments by those of skill in the art, without departing from the scope of the invention which is defined solely by the claims appended hereto.

We claim:

1. A method of treating melanoma cells in vitro comprising the steps of:
   (a) reducing TYRP2 in melanoma cells in vitro by contacting the cells in vitro with an antisense oligonucleotide targeting TYRP2 mRNA so that expression of TYRP2 is reduced; and
   (b) administering an anti-cancer therapy to the cells.

2. The method of claim 1, wherein the antisense oligonucleotide is a phosphorothioated antisense oligonucleotide targeting the TYRP2 ATG translation initiation codon.

3. The method of claim 1, wherein the antisense oligonucleotide is selected from the group consisting of SEQ ID NO:1 to SEQ ID NO:10.

4. The method of claim 1 wherein step a) comprises transfecting melanoma cells with an expression vector containing antisense TYRP2 cDNA.

5. The method of claim 1, wherein the anti-cancer therapy is selected from the group consisting of a chemotherapeutic agent and ionizing radiation.

6. The method of claim 5, wherein the anti-cancer therapy is a chemotherapeutic agent selected from the group consisting of alkylating agents, anti-metabolites, antibiotics, anti-microtubule agents and combinations thereof.

7. The method of claim 6, wherein the chemotherapeutic agent is selected from the group consisting of cis-diamminedichloroplatinum(II) (CDDP), carboplatin, methotrexate, and combinations thereof.

8. The method of claim 5, wherein the anti-cancer therapy is an ionizing radiation selected from the group consisting of UV(B) irradiation, gamma radiation, alpha particles, beta particles, x-rays and electron beams.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Antisense
      Oligonucleotide derived from TYRP2.

<400> SEQUENCE: 1
tccaccgtca tgcagactcg                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Antisense
      Oligonucleotide derived from TYRP2.

<400> SEQUENCE: 2
taggctgtcc accgtcatgc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Antisense
      Oligonucleotide derived from TYRP2.

<400> SEQUENCE: 3
tcactaggct gtccaccgtc                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Antisense
      Oligonucleotide derived from TYRP2.

<400> SEQUENCE: 4
gacattggcc gactctgcac                                              20

<210> SEQ ID NO 5
<211> LENGTH: 20
<212> TYPE: DNA
```

```
<213> ORGANISM: Artificial Sequence
<220> FEATURE:
<223> OTHER INFORMATION: Description of Artificial Sequence: Antisense
      Oligonucleotide derived from TYRP2.

<400> SEQUENCE: 5
atgcaggtcc ttgatgtgag                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Antisense
      Oligonucleotide derived from TYRP2.

<400> SEQUENCE: 6
ctaatcagag tcggatcgct                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Antisense
      Oligonucleotide derived from TYRP2.

<400> SEQUENCE: 7
atcattggcg gctgaatgtg                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Antisense
      Oligonucleotide derived from TYRP2.

<400> SEQUENCE: 8
gctgtagcca agttggtctg                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Antisense
      Oligonucleotide derived from TYRP2.

<400> SEQUENCE: 9
ctcttaggta aggcatgagc                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Antisense
      Oligonucleotide derived from TYRP2.

<400> SEQUENCE: 10
ttgtcagcgt cagaactgtg                                                    20
```